United States Patent
Jo et al.

(10) Patent No.: US 10,032,272 B2
(45) Date of Patent: Jul. 24, 2018

(54) WORKSTATION, MEDICAL IMAGING APPARATUS INCLUDING THE SAME, AND CONTROL METHOD FOR THE SAME

(71) Applicant: Samsung Electronics Co., Ltd., Suwon-si (KR)

(72) Inventors: Hyun Hee Jo, Suwon-si (KR); Seon Mi Park, Suwon-si (KR); Je Yong Shin, Suwon-si (KR); Se Jin Yoo, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 86 days.

(21) Appl. No.: 15/051,039

(22) Filed: Feb. 23, 2016

(65) Prior Publication Data
US 2017/0046848 A1    Feb. 16, 2017

(30) Foreign Application Priority Data
Aug. 11, 2015 (KR) .................. 10-2015-0113187

(51) Int. Cl.
| | |
|---|---|
| G06K 9/00 | (2006.01) |
| G06T 7/00 | (2017.01) |
| G06T 7/12 | (2017.01) |
| G06T 7/149 | (2017.01) |
| A61B 6/03 | (2006.01) |

(52) U.S. Cl.
CPC .............. *G06T 7/0012* (2013.01); *G06T 7/12* (2017.01); *G06T 7/149* (2017.01); *A61B 6/032* (2013.01); *G06T 2207/10081* (2013.01); *G06T 2207/10088* (2013.01); *G06T 2207/20116* (2013.01); *G06T 2207/30004* (2013.01); *G06T 2207/30024* (2013.01)

(58) Field of Classification Search
None
See application file for complete search history.

(56) References Cited

U.S. PATENT DOCUMENTS

| | | | |
|---|---|---|---|
| 2011/0245650 A1 | 10/2011 | Kerwin et al. | |
| 2013/0279764 A1 | 10/2013 | Codella et al. | |
| 2015/0078640 A1* | 3/2015 | Guo ...................... | G06T 7/0083 382/131 |

FOREIGN PATENT DOCUMENTS

| | | |
|---|---|---|
| DE | 102008015292 | 9/2009 |
| JP | 2001-202507 | 7/2001 |
| JP | 2013-255664 | 12/2013 |
| KR | 10-1996-0009732 | 3/1996 |

(Continued)

OTHER PUBLICATIONS

Extended European Search Report dated Dec. 21, 2016 in European Patent Application No. 16158624.3.

(Continued)

*Primary Examiner* — Atiba O Fitzpatrick
(74) *Attorney, Agent, or Firm* — Staas & Halsey LLP

(57) ABSTRACT

A workstation, a medical imaging apparatus including the same, and a control method for the same includes an input unit that receives information about a contour of an organ in a medical image obtained by imaging a subject and a control unit that corrects the contour of the organ in such a manner that the contour of the organ does not cross contours of one or more other organs located inside or outside the organ.

19 Claims, 29 Drawing Sheets

(56) References Cited

FOREIGN PATENT DOCUMENTS

KR           10-1404345       6/2014
KR    10-2015-0054738       5/2015

OTHER PUBLICATIONS

Zhen Ma, et al. "Novel Approach to Segment the Inner and Outer Boundaries of the Bladder Wall in T2-Weighted Magnetic Resonance Images", Annals of Biomedical Engineering, vol. 39, No. 8, Aug. 2011, pp. 2287-2297.
Korean Notice of Allowance dated Sep. 18, 2017 in Korean Patent Application No. 10-2015-0113187.
Korean Office Action dated Jul. 1, 2017 in Korean Patent Application No. 10- 2015-0113187.

\* cited by examiner

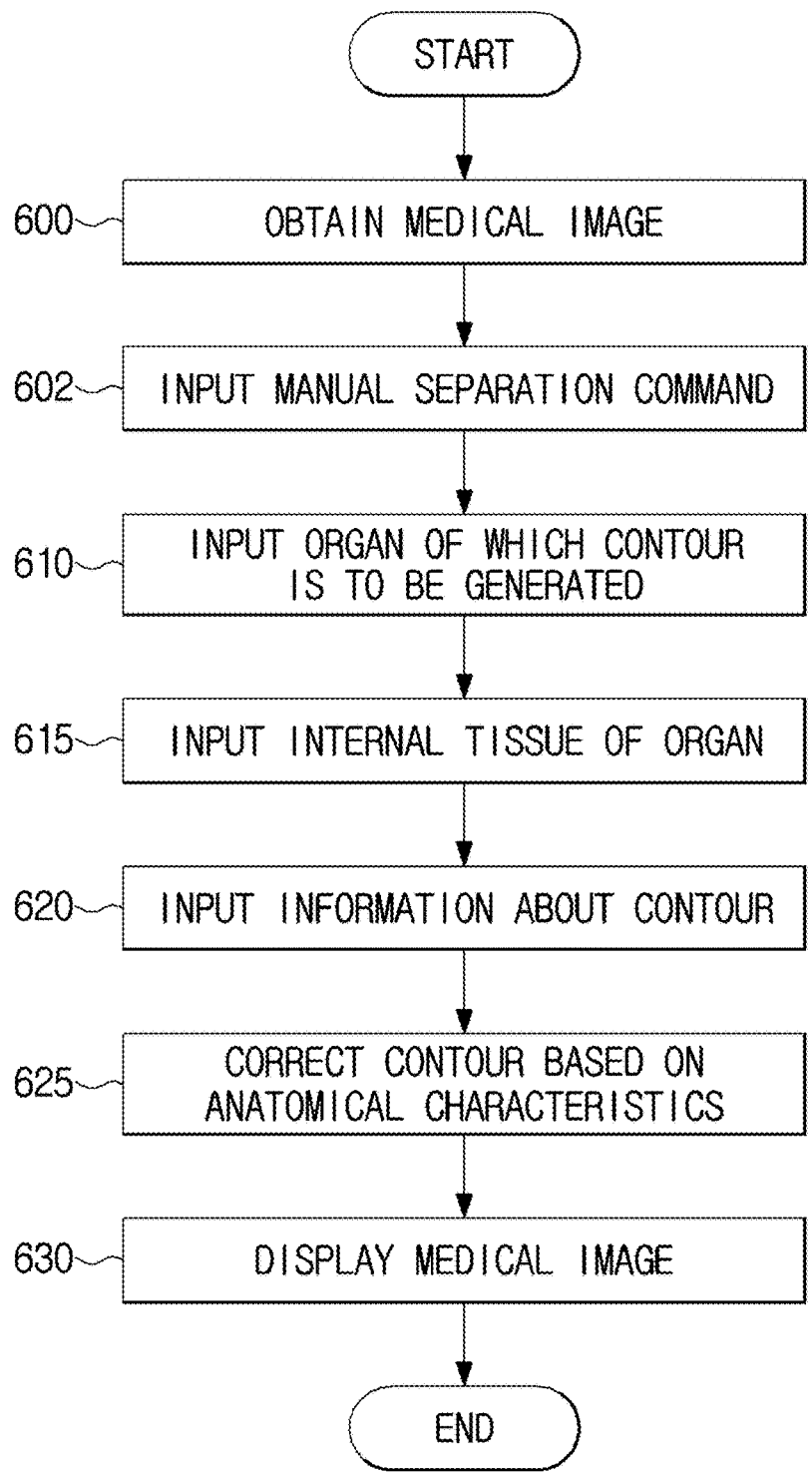

WORKSTATION, MEDICAL IMAGING APPARATUS INCLUDING THE SAME, AND CONTROL METHOD FOR THE SAME

CROSS-REFERENCE TO RELATED APPLICATIONS

This application claims the priority benefit of Korean Patent Application No. 10-2015-0113187, filed on Aug. 11, 2015 in the Korean Intellectual Property Office, the disclosure of which is incorporated herein by reference.

BACKGROUND

1. Field

The following description relates to a workstation that manages a medical image obtained by imaging the inside of a subject, a medical imaging apparatus including the same, and a control method for the same.

2. Description of the Related Art

In general, a medical imaging apparatus is a device that obtains a medical image by imaging the inside of a subject so that the obtained medical image can be used in a diagnosis. In this instance, for more accurate diagnosis from the medical image, accurate determination of organs in the medical image is required. Thus, the contours of the organs are drawn in the medical image through a separation process, and a diagnosis of the corresponding organ is generally made based on the drawn contours. However, a lot of time and effort is required in order to accurately generate the contour of the organ, and research to more quickly and accurately generate the contour of the organ is ongoing.

SUMMARY

Therefore, it is an aspect of the present disclosure to provide a workstation, a medical imaging apparatus including the same, and a control method for the same.

Additional aspects of the disclosure will be set forth in part in the description which follows and, in part, will be obvious from the description, or may be learned by a practice of the disclosure.

In accordance with an aspect of the present disclosure, a workstation includes an input unit that receives information about a contour separating one or more organs in a medical image obtained by imaging a subject; and a control unit that performs correction in such a manner that the contours do not cross each other, when the contour is generated based on the received information about the contour.

Here, the control unit may perform a correction in such a manner that the contour of the organ and a contour of internal tissue of the organ, and one or more contours among contours of one or more other organs are in contact with one another based on anatomical characteristics.

Also, the control unit may correct a second contour in such a manner that the second contour does not cross an already generated first contour among the contours based on anatomical characteristics, or correct the second contour in such a manner that a part of the second contour does not cross the already generated first contour, or correct the second contour in such a manner that the other part of the second contour is in contact with the already generated first contour.

Also, the input unit may receive information about the organ for which the contour is to be generated or information about an outer wall or an inner wall of the organ for which the contour is to be generated.

Also, when an inner wall or an outer wall of the organ is present, the control unit may correct a contour of the inner wall in such a manner that the contour of the inner wall does not cross a contour of the outer wall.

Also, when the contour of the inner wall is drawn outside the contour of the outer wall, the control unit may delete the contour of the inner wall.

Also, when the contours cross each other, the control unit may perform a correction based on a separation distance input from a user.

Also, the control unit may perform a correction based on an average separation distance between the contours within the medical image, or perform s correction based on an average separation distance stored in a database.

Also, when the contour of the inner wall crosses the contour of the outer wall, the control unit may perform a correction based on information about a separation distance input from a user.

Also, when the contour of the inner wall crosses the contour of the outer wall, the control unit may perform a correction based on an average separation distance between the contour of the inner wall and the contour of the outer wall within the medical image or perform a correction based on an average separation distance stored in a database.

Also, the workstation may further include a communication unit that receives the medical image obtained from a medical imaging apparatus.

In accordance with an aspect of the present disclosure, a workstation includes: a control unit that performs a correction in such a manner that contours are not overlapped with one another, in a medical image in which the contours separating one or more organs are generated according to an automatic separation; and a display unit that displays the medical image corrected by the control unit.

Here, when the contours are overlapped with one another, the control unit may simultaneously correct the overlapped contours or corrects only the contour selected from the overlapped contours.

Also, the control unit may perform correction in such a manner that the contours are in contact with one another based on anatomical characteristics or perform a correction based on a preset separation distance.

Also, the control unit may correct a second contour in such a manner that the second contour does not cross an already generated first contour among the contours based on anatomical characteristics, correct the second contour in such a manner that a part of the second contour does not cross the already generated first contour, or correct the second contour in such a manner that the other part of the second contour is in contact with the already generated first contour.

Also, the control unit may perform a correction based on a separation distance input from a user, based on an average separation distance between organs within the medical image, or based on an average separation distance stored in a database.

Also, when any one of the contours relates to an inner wall of the organ and the other of the contours relates to an outer wall of the organ, the control unit may perform a correction in such a manner that a contour of the inner wall does not cross a contour of the outer wall.

Also, when the contour of the inner wall is drawn outside the contour of the outer wall, the control unit may delete the contour of the inner wall.

Also, when the contour of the inner wall crosses the contour of the outer wall, the control unit may perform a correction based on information about a separation distance input from a user.

Also, when the contour of the inner wall crosses the contour of the outer wall, the control unit may perform a correction based on an average separation distance between the contour of the inner wall and the contour of the outer wall within the medical image or based on an average separation distance stored in a database.

In accordance with an aspect of the present disclosure, a medical imaging apparatus includes: an imaging unit that obtains a medial image of an organ of a subject; a display unit that displays the medical image obtained by the imaging unit; an input unit that receives information about a contour separating one or more organs; and a control unit that performs a correction in such a manner that the contours do not cross one another, when the contour is generated based on the received information about the contour.

In accordance with an aspect of the present disclosure, a medical imaging apparatus includes: an imaging unit that obtains a medical of about an organ of a subject; a control unit that performs a correction in such a manner that contours are not overlapped with one another when the contour separating one or more organs is generated according to an automatic separation in the medical image; and a display unit that displays the medical image corrected by the control unit.

In accordance with an aspect of the present disclosure, a method of controlling a workstation includes: receiving a generation command for a contour; receiving one or more organs to be separated according to the received generation command for the contour; receiving information about the contour of the received one or more organs; and correcting the contour in such a manner that the contours generated from the received information about the contour do not cross each other.

Here, when the contour of any one organ among the contours crosses the contour of another organ located in the vicinity of the organ, the correcting of the contour may include correcting the contour in such a manner that the contour of the organ and the contour of the other organ are in contact with each other based on anatomical characteristics or correcting the contour according to a preset separation distance.

Also, the receiving of the one or more organs may further include receiving one of an inner wall and an outer wall of the organ for which the contour generation is intended.

Also, when a contour of the inner wall of the organ crosses a contour of the outer wall, the correcting of the contour may include correcting the contour in such a manner that the contour of the inner wall and the contour of the outer wall of the organ are in contact with each other based on anatomical characteristics or correcting the contour according to a preset separation distance.

Also, when the contour of the inner wall is drawn outside the contour of the outer wall, the correcting of the contour may include deleting the contour of the inner wall of the organ.

Also, when a plurality of organs of which contours are drawn are provided within the medical image, the correcting of the contour may include simultaneously correcting overlapped contour regions between the plurality of organs or correcting only the contour selected by a user.

In accordance with an aspect of the present disclosure, a method of controlling a workstation includes: correcting a contour in such a manner that the contours are not overlapped with one another in a medical image of which the contour separating one or more organs is drawn according to an automatic separation; and displaying the corrected medical image.

Here, when the contours are overlapped with one another, the correcting of the contour may include simultaneously correcting the overlapped contours or correcting only the contour selected among the overlapped contours.

Also, the correcting of the contour may include correcting the contour in such a manner that the contours are in contact with one another based on anatomical characteristics or correcting the contour based on a preset separation distance.

Also, when a contour of an inner wall of any one organ among the one or more organs is drawn outside a contour of an outer wall of the organ, the correcting of the contour may include deleting the contour of the inner wall.

BRIEF DESCRIPTION OF THE DRAWINGS

These and/or other aspects of the disclosure will become apparent and more readily appreciated from the following description of the embodiments, taken in conjunction with the accompanying drawings of which:

FIGS. 6A and 6B illustrate the operation of a medical imaging apparatus in accordance with an embodiment of the present disclosure;

DETAILED DESCRIPTION

Figure 1:
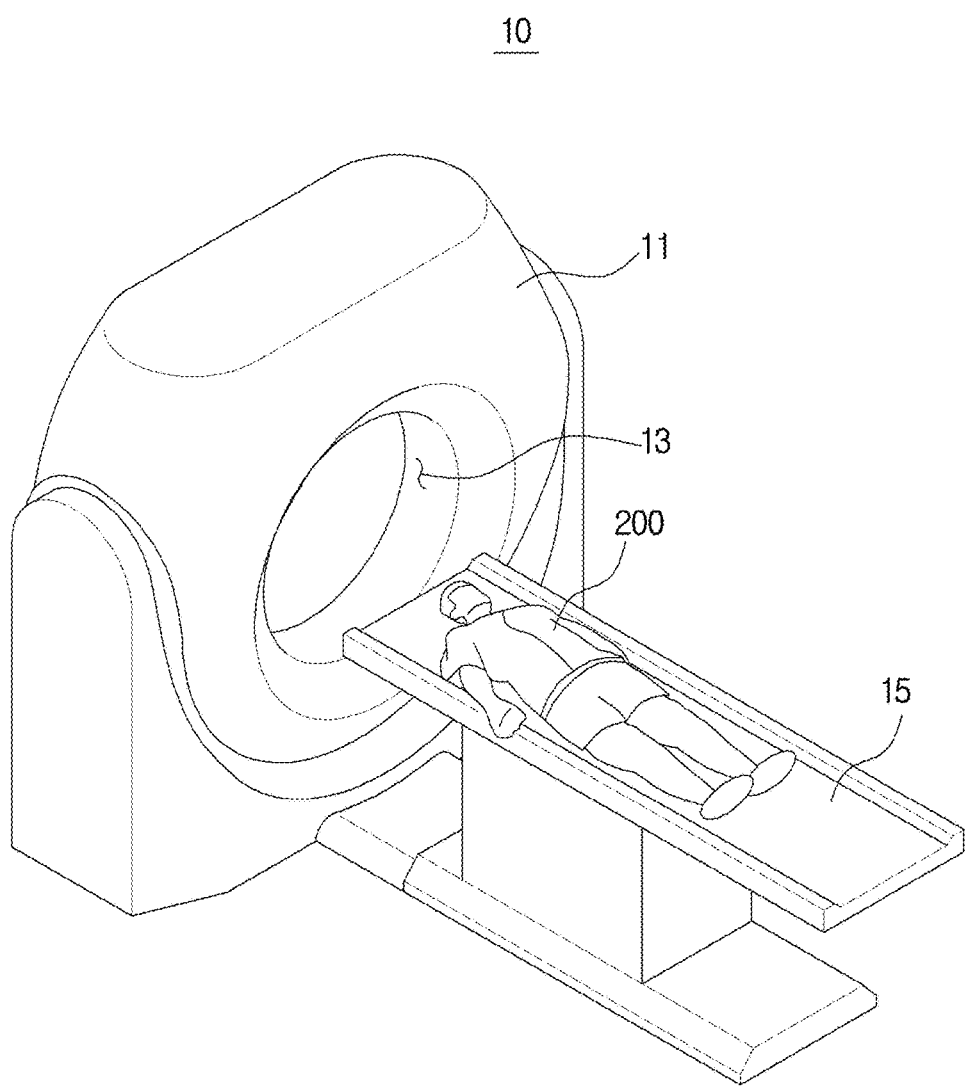
FIG. 1 illustrates the appearance of a CT (computed tomography) apparatus as an example of a medical imaging apparatus.

Hereinafter, embodiments of the present disclosure will be described in detail with reference to the accompanying drawings, wherein like reference numerals refer to like elements throughout. The embodiments are described below to explain the present disclosure by referring to the figures.

FIG. 1 illustrates the appearance of a CT (computed tomography) apparatus as an example of a medical imaging apparatus.

The medical imaging apparatus refers to an apparatus that obtains a medical image by imaging the inside of a subject. Here, the subject may be a living body of a human or animal, but is not particularly limited thereto. Any subject may be applied as long as its internal structure can be imaged by a variety of signals irradiated by the medical imaging apparatus.

The medical imaging apparatus which will be described below includes all types of apparatuses that obtain medical images obtained by imaging the inside of the subject. According to an embodiment, the medical imaging apparatus includes a CT apparatus 10 as illustrated in FIG. 1.

Referring to FIG. 1, the CT apparatus 10 performs a scan of a subject 200 by a gantry 11 with a bore 13 formed at the center thereof. Inside the gantry 11, an X-ray source for generating and irradiating X-rays and an X-ray detector for detecting X-rays transmitted through the subject are mounted to face each other. A subject 200 is transferred into the bore 13 while lying on a patient table 15, and when a scan portion of the subject 200 is located in a scan position, the X-ray source and the X-ray detector inside the gantry 11 irradiate and detect X-rays while rotating, thereby scanning the subject 200. Thus, the CT apparatus 10 may obtain a medical image based on the scan result.

Figure 2:
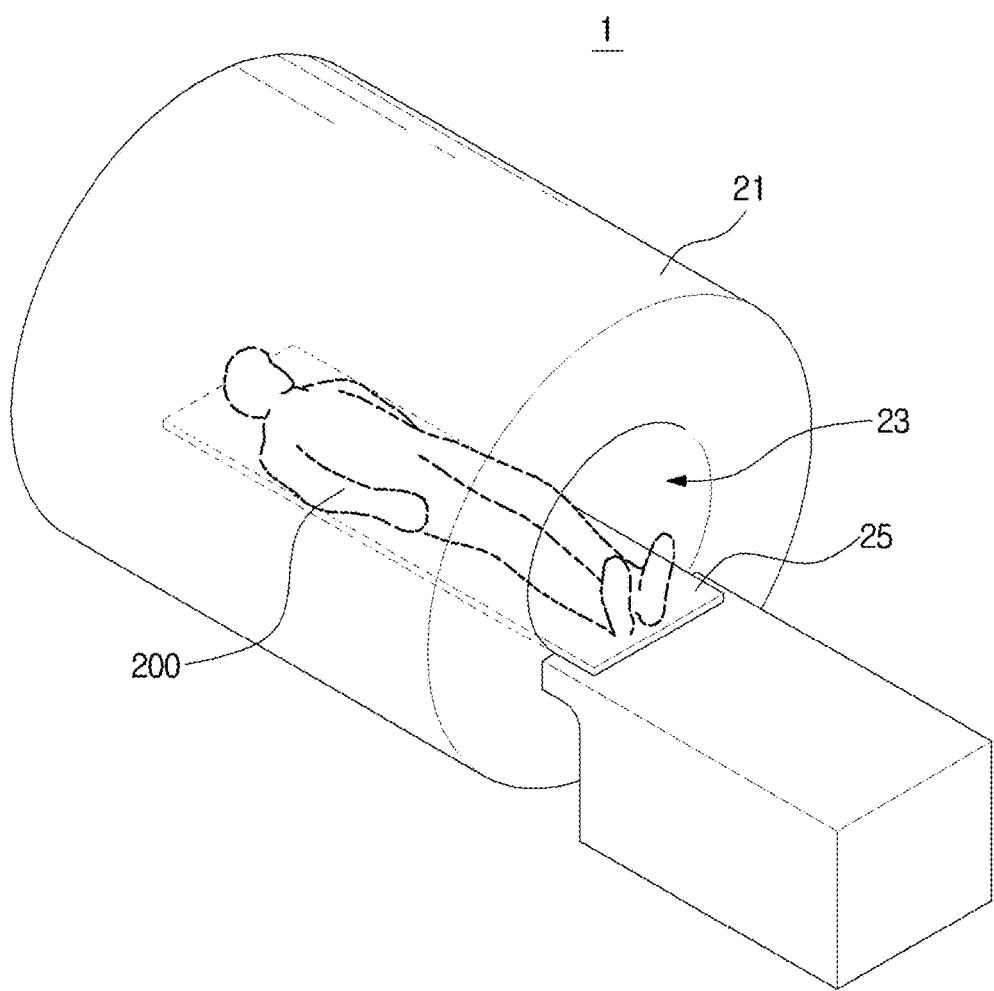
FIG. 2 illustrates the appearance of an MRI (magnetic resonance imaging) apparatus as an example of a medical imaging apparatus.

The medical imaging apparatus is not limited to the above-described embodiment and may include all types of apparatuses which can obtain medical images of the inside of the subject, such as an MRI (magnetic resonance imaging) apparatus of FIG. 2, an ultrasonic imaging apparatus using a ultrasonic probe, and the like.

Hereinafter, an MRI apparatus will be described as an example of the medical imaging apparatus, but embodiments which will be described below are not limited thereto, and any apparatus may be applied as long as the apparatus can obtain a medical image.

Figure 3:
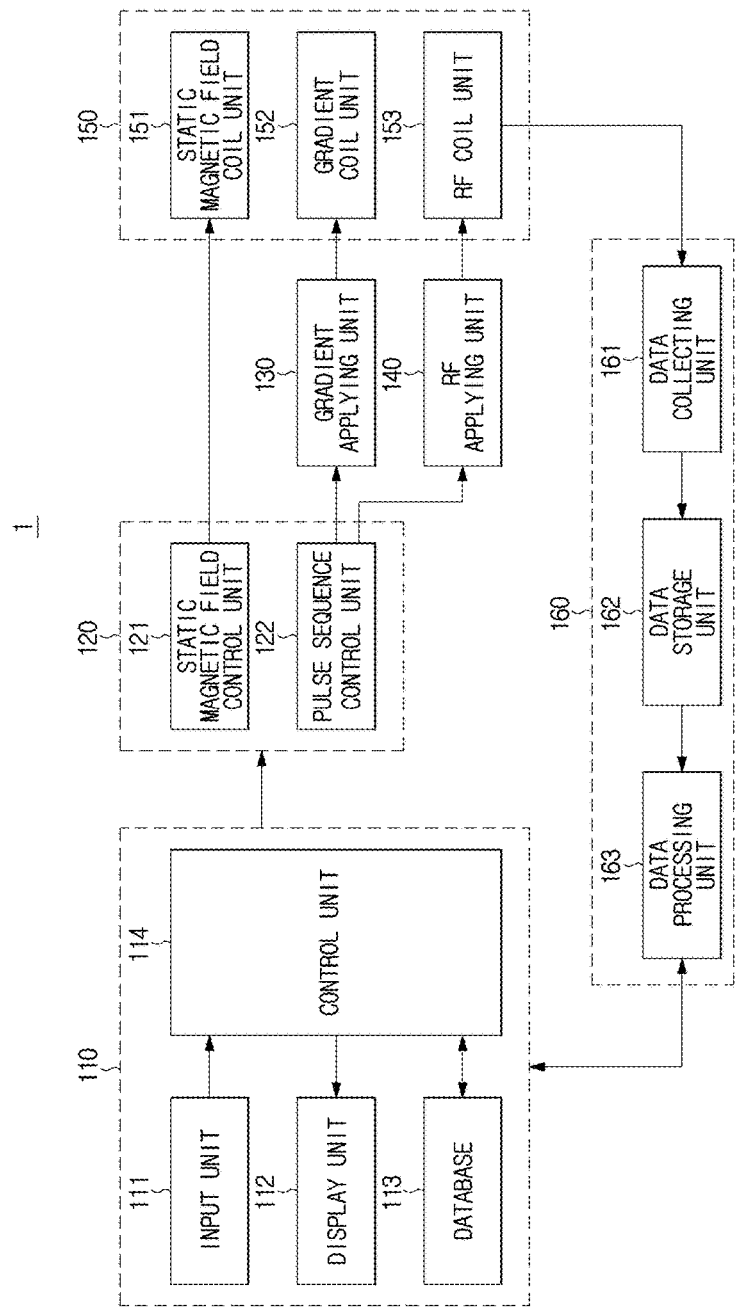
FIG. 3 is a control block diagram illustrating a medical imaging apparatus in accordance with an embodiment of the present disclosure.
Figure 4:
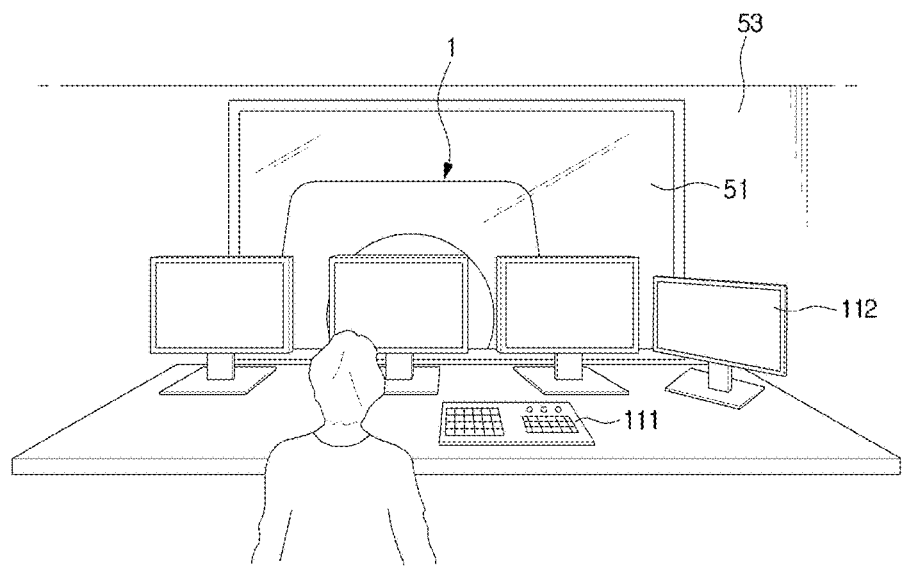
FIG. 4 illustrates a work space in which a workstation is provided in accordance with an embodiment of the present disclosure.
Figure 5A:
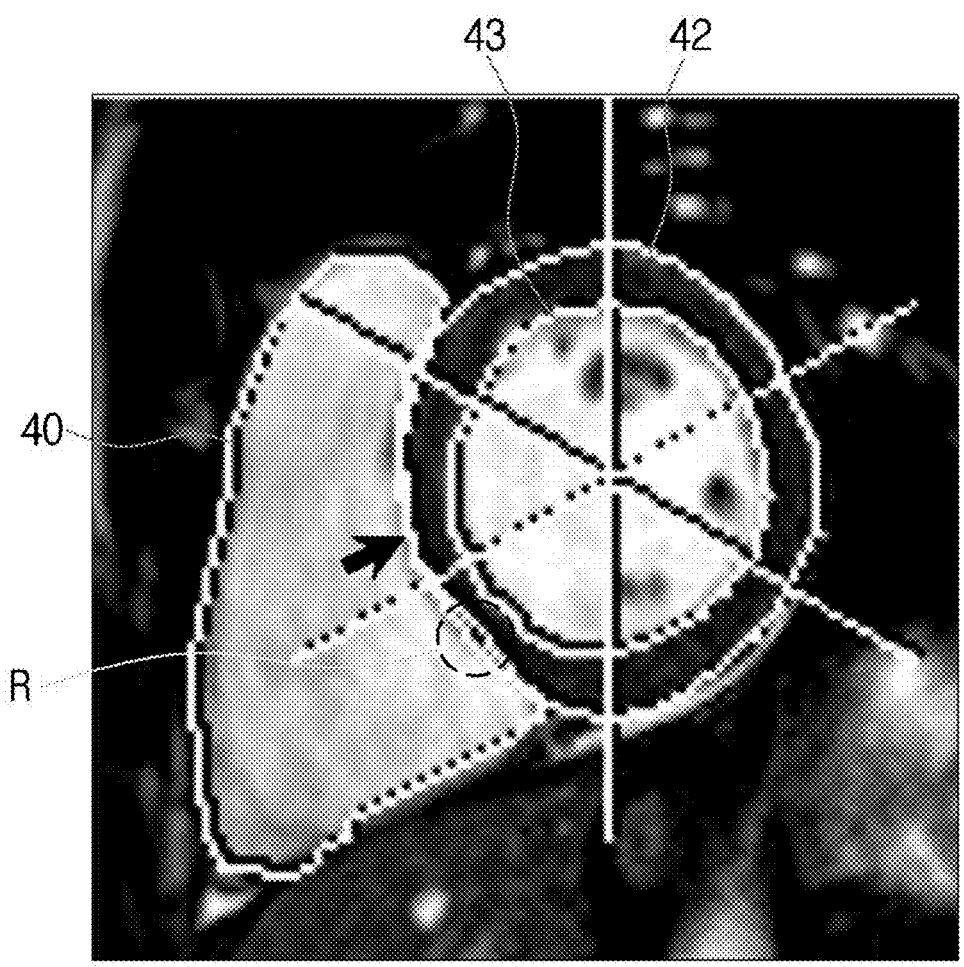
FIGS. 5A, 5B, and 5C illustrate a medical image of which a contour is generated according to an automatic separation or a manual separation in accordance with an embodiment of the present disclosure.
Figure 5B:
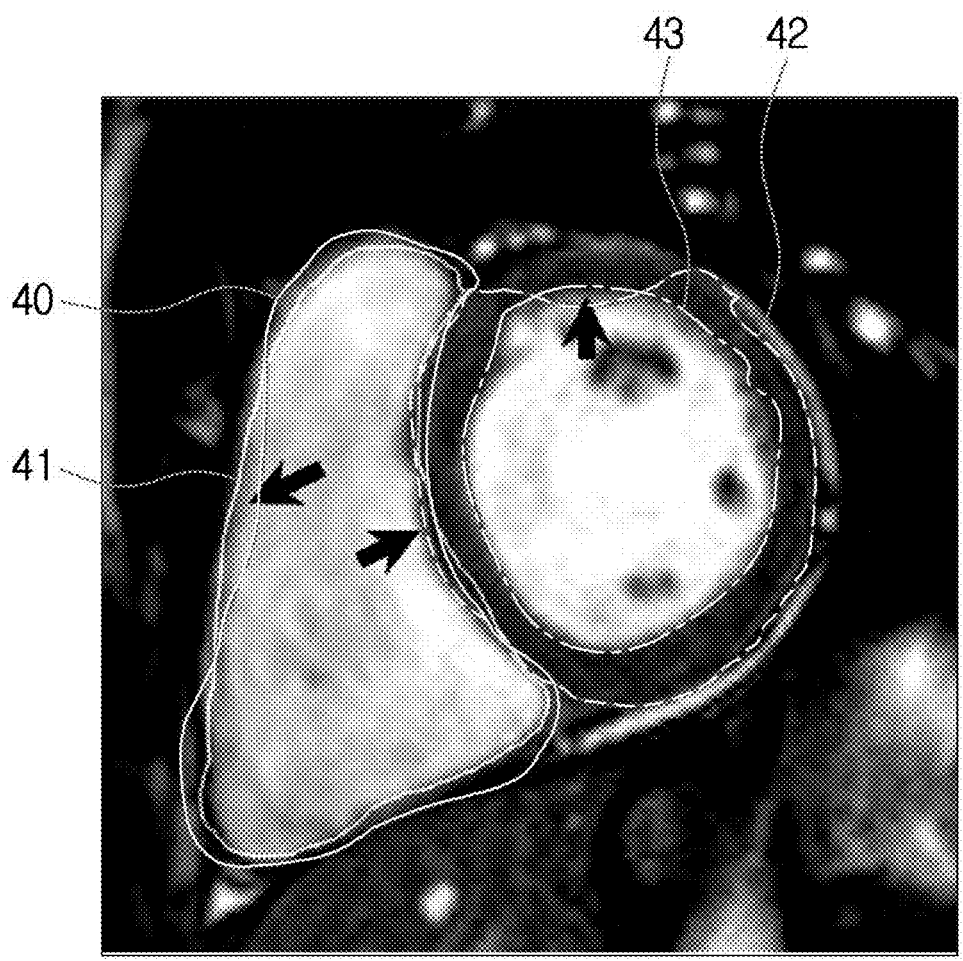
Figure 5C:
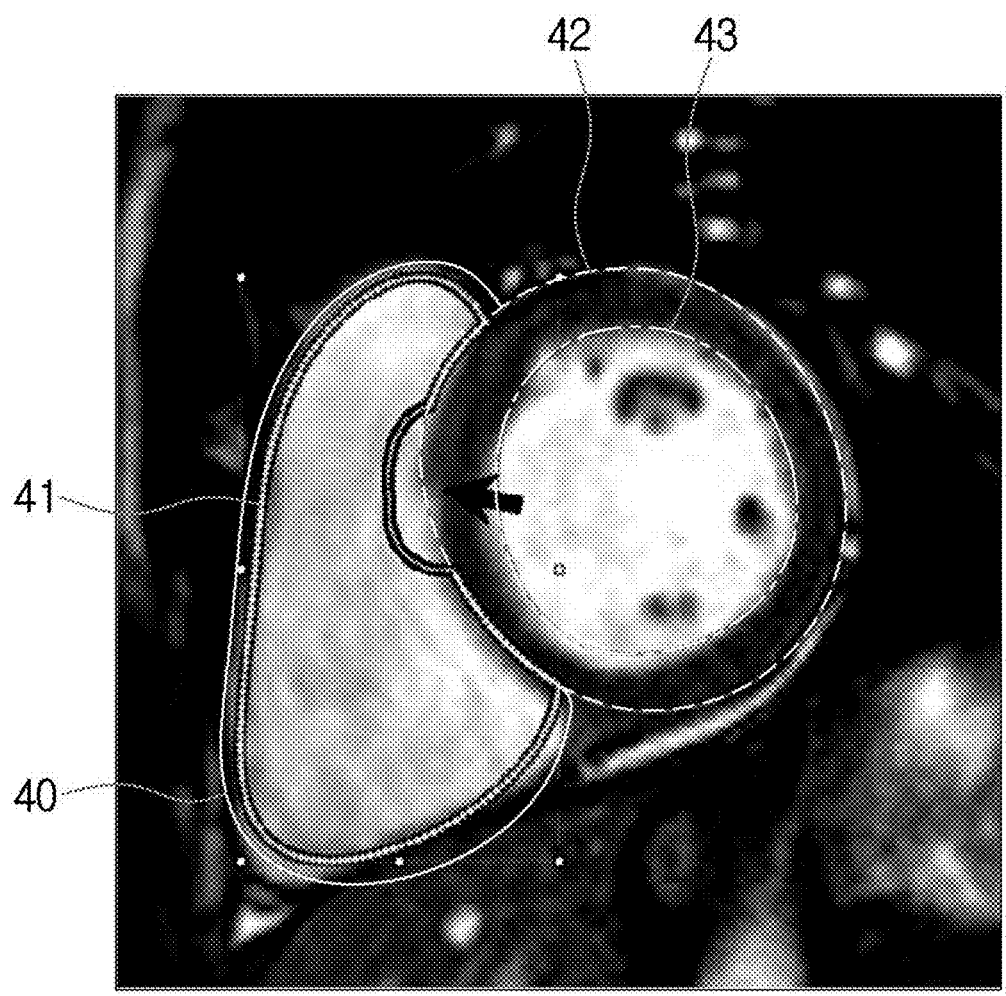

FIG. 2 illustrates the appearance of an MRI apparatus as an example of a medical imaging apparatus, FIG. 3 is a control block diagram illustrating a medical imaging apparatus in accordance with an embodiment of the present disclosure, FIG. 4 illustrates a work space in which a workstation is provided in accordance with an embodiment of the present disclosure, and FIG. 5 illustrates a medical image of which a contour is generated according to an automatic separation or a manual separation in accordance with an embodiment of the present disclosure.

Referring to FIG. 2, the medical imaging apparatus 1 performs a scan of a subject 200 by a gantry 21 with a bore 23 formed at the center thereof. A magnet assembly producing a magnetic field in the bore 23 is mounted inside the gantry 21, and when the subject 200 is transferred into the bore 23 while lying on a patient table 25, the magnet assembly mounted in the gantry 21 produces a magnetic field inside the bore 25 and scans the subject 200. Accordingly, the medical imaging apparatus 1 may obtain a medical image of the inside of the subject 200.

More specifically, the medical imaging apparatus 1 includes a magnet assembly 150 that produces a magnetic field and generates a resonance phenomenon for atomic nuclei, a magnet control unit 120 that controls the operation of the magnet assembly 150, an image processing unit 160 that receives an echo signal generated from the atomic nuclei and generates a medical image, a workstation 110 that controls the overall operations of the medical imaging apparatus 1, and the like, as illustrated in FIG. 3.

The magnet assembly 150 includes a static magnetic field coil unit 151 that produces a static magnetic field, a gradient coil unit 152 that produces a gradient magnetic field in the static magnetic field, and an RF (radio frequency) coil unit 153 that excites the atomic nuclei by applying an RF pulse and receives an echo signal from the atomic nuclei.

The magnet control unit 120 includes a static magnetic field control unit 121 that controls the intensity and direction of the static magnetic field produced by the static magnetic field coil unit 151 and a pulse sequence control unit 122 that designs a pulse sequence and controls the gradient coil unit 152 and the RF coil unit 153 according to the designed pulse sequence.

The medical imaging apparatus 1 includes a gradient applying unit 130 that applies a gradient signal to the gradient coil unit 152 and an RF applying unit 140 that applies an RF signal to the RF coil unit 153, and the pulse sequence control unit 122 may adjust the gradient magnetic field produced in the static magnetic field and the RF applied to the atomic nuclei by controlling the gradient applying unit 130 and the RF applying unit 140.

The gradient coil unit 152 produces a gradient magnetic field by generating a gradient in the static magnetic field produced in the bore. In order to obtain three-dimensional (3D) spatial information, the gradient magnetic fields for x-axis, y-axis, and z-axis are required, so the gradient coil unit 152 includes three pairs of gradient coils.

The static magnetic field coil unit 151 is provided in the form in which a coil is wound around the bore, and when a current is applied to the static magnetic field coil unit 151, the static magnetic field is produced inside the magnet assembly 150, that is, in the bore. The direction of the static magnetic field is generally parallel to the same axis of the magnet assembly 150.

When the static magnetic field is produced in the bore, the atomic nuclei of atoms constituting the subject 200, particularly, hydrogen atoms, are aligned in a direction of the static magnetic field, and are subjected to a precession movement around the direction of the static magnetic field. The precession speed of the atomic nuclei may be represented by a precession frequency. For example, the hydrogen protons have a precession frequency of 42.58 MHz in the external magnetic field of 1 T, and the hydrogen atoms occupy the largest percentage of atoms constituting the human body, so that the MRI apparatus may mainly obtain a magnetic resonance signal using the precession of the hydrogen protons.

Here, the RF coil unit 153 includes a transmission coil that transmits an RF pulse and a reception coil that receives an electromagnetic wave emitted by the excited atomic nuclei, that is, a magnetic resonance signal. The RF coil unit 153 is connected to the RF applying unit 140, and the RF applying unit 140 applies a driving signal to the RF coil unit 153 according to a control signal transmitted from the pulse sequence control unit 122 and transmits the RF pulse.

The RF applying unit 140 may include a modulation circuit that modulates a high-frequency output signal into a pulsed signal and an RF power amplifier that amplifies the pulsed signal. In addition, the RF coil unit 153 is connected to the image processing unit 160, and the image processing unit 160 includes a data collecting unit 161 that receives data about the magnetic resonance signal generated from the atomic nuclei and a data processing unit 163 that generates a medical image by processing the data received by the data collecting unit 161.

The data collecting unit 161 includes a preamplifier that amplifies the magnetic resonance signal received by the reception coil of the RF coil unit 153, a phase detector that receives the magnetic resonance signal from the preamplifier and detects a phase, and an ND (analog/digital) converter that converts an analog signal obtained by the phase detection into a digital signal. The data collecting unit 161 transmits the digital-converted magnetic resonance signal to a data storage unit 162.

A data space constituting a two-dimensional Fourier space is formed in the data storage unit 162, and when the storage of the entire scanned data is completed, the data processing unit 163 performs a two-dimensional inverse Fourier transform on the data within the two-dimensional Fourier space, thereby reconstituting the medical image of the subject 200. The reconstituted medical image is displayed on a display unit 112 of the workstation 110.

The workstation 110 may receive a variety of control commands about the medical imaging apparatus 1 from a user and control the operation of the medical imaging apparatus 1 based on the received control commands. In addition, the workstation 110 may obtain a variety of results required for the diagnosis by processing a variety of processes such as editing, correcting, and the like of the medical image. Here, the workstation 110 may be referred to as a host device or a console, but, for convenience of description in the embodiment which will be described below, a device that controls the overall operations of the medical imaging apparatus 1 is referred to as the workstation 110.

Meanwhile, some devices of the medical imaging apparatus 1 may be separately provided in a scan room in which a scan of the subject 200 is performed and a control room that controls the scan of the subject 200. Accordingly, a user may obtain desired information from the scan of the subject 200 in the control room as well as the image processing of the obtained medical image.

For example, the workstation 110 may be provided in a separate work space. Referring to FIG. 4, in the medical imaging apparatus 1, the scan room in which the gantry is positioned and a scan of the subject is performed and the control room in which control of a user is performed may be separated from each other by a shielding wall 53 and a shielding glass 51.

However, the workstation 110 is not provided only in the control room, and a process for controlling the scan of the subject may be performed in the control room and the subsequent image process may be performed in a separate room. In this instance, the workstation 110 provided in the control room corresponds to a first workstation, and the workstation provided in the separate room corresponds to a second workstation. Hereinafter, the workstation 110 which will be described below includes at least one of the first workstation and the second workstation.

A user may obtain a medical image in which a contour of an organ is drawn using the workstation 110. For example, in the case of a heart as one of the organs, it is required to accurately distinguish the heart muscles of the left ventricle and the right ventricle from several hundreds of medical images in order to quantitatively analyze the function of the heart. Accordingly, by determining changes in each of the muscles of heart from a plurality of medical images, a quantitative analysis is possible by analyzing the characteristics of heart, blood flow and the like, and therefore it is possible to diagnose heart diseases.

Referring to FIG. 3, the workstation 110 includes an input unit, or interface, 111, a display unit, or display, 112, a DB (database) 113, and a control unit, or controller, 114. The DB 113 and the control unit 114 may be integrated in an SOC (system on chip) built in the workstation 110. In this instance, a plurality of SOCs rather than one SOC which is built in the workstation 110 may be present, and therefore the present disclosure is not limited to a case in which the DB 113 and the control unit 114 are integrated in only one SOC.

The input unit 111 may receive a control command about the overall operations of the medical imaging apparatus 1 from a user. In addition, the input unit 111 may receive a variety of commands relating to a separation process of the medical image. For example, the input unit 111 may receive a separation command such as an automatic separation command or a manual separation command, and the like. In addition, the input unit 111 may receive information about an organ to be separated or an internal structure of the organ, and the like from a user.

When receiving the manual separation command, that is, a contour generation command, the input unit 111 may receive information about the contour using a manual separation tool from a user. The manual separation tool may support the user input of the information about the contour and be implemented by software. As will be described later, the manual separation tool may be stored in the DB 113 of the medical imaging apparatus 1. Here, the information about the contour may be used for setting a contour separating the corresponding organ and includes things that can be set to divide the corresponding organ, such as a point, or a line, for example.

As an embodiment, the input unit 111 may receive the information about the contour through the manual separation tool such as point marking or freehand. In this instance, the information about the contour is not limited by the embodiment, and the contour may be set using a variety of known manual separation tools.

The input unit 111 may be implemented by a keyboard, a mouse, a joystick, a trackball, or the like, but is not limited thereto. The input unit 111 may be implemented by a variety of known devices that can receive a variety of commands from a user. Meanwhile, the control unit 114 may generate the contour based on the information about the contour received through the input unit 111.

The display unit 112 may display the medical image, so that the user may determine the health condition of the subject 200. In addition, the user may view the medical image displayed on the display unit 112 and input the information about the contour through the input unit 111.

The display unit 112 may be implemented as an LCD (liquid crystal display), an LED (light emitting diode) display, a PDP (plasma display panel), an OLED (organic light emitting diode) display, a CRT (cathode ray tube), or the like, but is not limited thereto. Meanwhile, when the display unit 112 is implemented in the form of a touch screen, the display unit 112 may also perform the function of the input unit 111.

A variety of data relating to the editing of the medical image may be stored in the DB 113. For example, software implementing an automatic separation algorithm may be stored in the DB 113. In addition, software providing a manual separation tool may be stored.

Meanwhile, a variety of data relating to the internal organs of the subject may be stored in the DB 113. For example, a relative positional relationship between organs and a relative positional relationship between internal tissues of the organ are different from each other depending on the anatomical characteristics. Anatomical characteristic data for each organ may be stored in the DB 113, and as will be described later, the control unit 114 may correct the contour based on the stored anatomical characteristic data.

The DB 113 may be implemented through at least one type of memory among a flash memory type memory, a hard disk type memory, a multimedia card micro type memory, a card type memory (e.g., SD or XD memory, etc.), a RAM (random access memory), an SRAM (static random access memory), a ROM (read-only memory), an EEPROM (electrically erasable programmable read-only memory), a PROM (programmable read-only memory), a magnetic memory, a magnetic disk, and an optical disk. However, the DB 113 is not limited thereto, and it may be implemented in any other form known in the art.

The control unit 114 may control the overall operations of the medical imaging apparatus 1. For example, the control unit 114 may generate a control signal for controlling components of the medical imaging apparatus 1 and control the operation of each of the components of the medical imaging apparatus 1. According to an embodiment, the control unit 114 may display the medical image by controlling the operation of the display unit 112 based on the control command input from the input unit 111.

The control unit 114 may generate the contour of the organ through the separation process. As examples of a method of generating the contour through the separation process, an automatic separation method and a manual separation method may be given. Here, the manual separation method is a method of generating the contour based on the information about the contour received from a user using a manual separation tool such as point marking or freehand. The automatic separation method is a method of receiving an automatic separation command from a user or automatically generating the contour from the medical image.

The automatic separation method has an advantage of having a speed faster than that of the manual separation method. However, when the contour is generated through the automatic separation method, time for verification and correction is further required due to an accuracy lower than that in the manual separation method.

For example, in a case of the structure of the heart, there should be no overlapped region between contours of the left ventricle and the right ventricle of the heart, and partial regions thereof should be in contact with one another so that there is no empty region. In addition, a contour of the inner wall of the left ventricle should be drawn within a contour of the outer wall of the left ventricle. FIG. 5A illustrates a medical image in which contours of the left ventricle and the right ventricle of the heart are generated through an automatic separation process. Although partial regions of a contour 40 of the outer wall of the left ventricle and a contour 42 of the inner wall of the right ventricle are in contact with each other, an empty region R that is not in agreement with the anatomical structure is generated as illustrated in FIG. 5A. Accordingly, it is difficult for a user to accurately diagnose the heart using the contour illustrated in FIG. 5A.

FIG. 5B illustrates a medical image in which contours of the left ventricle and the right ventricle of the heart are generated through a manual separation process. As described above, the contours of the left ventricle and the right ventricle of the heart should not be overlapped with each other, and partial regions thereof should be in contact with one another so that there is no empty region.

In addition, a contour 43 of the inner wall of the left ventricle should be drawn within a contour 42 of the outer wall of the left ventricle, and a contour 41 of the inner wall of the right ventricle should be drawn within the contour 40 of the outer wall of the right ventricle. In this instance, specifically referring to FIG. 5B, a part of the contour 41 of the inner wall of the right ventricle is drawn outside the contour 40 of the outer wall of the right ventricle. In addition, a part of the contour 43 of the inner wall of the left ventricle is drawn outside the contour 42 of the outer wall of the left ventricle. Accordingly, using the contours 40, 41, 42, and 43 for the heart illustrated in the drawing, an accurate diagnosis of the heart cannot be obtained, and a correction of the contours is required.

In this instance, it takes a lot of time for a user to individually check and correct the contours. For example, it would take approximately 15 minutes to check and correct 22 pieces of medical images depending on user's skill. Thus, as described above, there is a disadvantage in that it would take too much labor and time to check and correct contours of 300 to 400 pieces of medical images, for example.

The medical imaging apparatus 1 according to the disclosed embodiment may perform a correction of the contour in consideration of the anatomical characteristics when a separation process is performed. Thus, the medical imaging apparatus 1 according to the disclosed embodiment may help in obtaining a more accurate diagnosis by increasing the accuracy of the separation and increase the user convenience by reducing the time required for the correction of the contour.

Meanwhile, a correction method which will be discussed in the following is not limited to the heart, and may be applied to all the organs such as the heart, the liver, the spleen, the stomach, etc. existing inside the subject, and a variety of internal tissues constituting the organs. That is, in addition to the contours of the outer wall and the perimeter of the organ, contours of the inner wall and internal tissues of the organ can also be drawn, and the correction method which will be discussed in the following can be applied to all of the above-described contours.

For example, in the case of the heart, the correction method according to the disclosed embodiment can be applied to all parts of the organ found in the medical image, such as the inner/outer walls of the left ventricle and the right ventricle constituting the heart, tumors which are possibly present in the heart, and the like.

The control unit 114 may generate the contour based on the anatomical characteristics. The control unit 114 may receive the information about the contour in response to the manual separation command and correct the contour by reflecting the anatomical characteristics when generating the contour based on the received information about the contour.

In addition, even when the contour is generated through the automatic separation process, the control unit 114 may correct the contour by reflecting the anatomical characteristics. In this instance, the control unit 114 may perform a correction of the contour by receiving a correction command from a user through the input unit 111 or automatically perform a correction of the contour and provide the correction result to the user.

Here, the anatomical characteristics refer to a relative positional relationship between different organs or a relative positional relationship between internal tissues of the organ, as well as the appearance, size, and location of the organ.

For example, the control unit 114 may generate a first contour and a second contour through the separation process. Here, the first contour may relate to the perimeter or outer wall of the organ, and the second contour may relate to the above-described internal tissues or inner wall of the organ. In this instance, due to the anatomical characteristics, the second contour should be generated to not cross the first contour. Alternatively, due to the anatomical characteristics, a part of the second contour does not cross the first contour, and the other part thereof should be generated to be in contact with the first contour. Thus, by way of an embodiment example, when the first contour is generated and then the second contour is generated, the control unit 114 may perform a correction in such a manner that the second contour does not cross the already generated first contour and partial regions of the second contour are in contact with the already generated first contour, according to the anatomical characteristics.

By way of an example, the first contour may relate to the perimeter or outer wall of the organ, and the second contour may relate to the perimeter or outer wall of another organ located in the vicinity of the above-described organ. In this instance, due to the anatomical characteristics, the second contour should be generated to not cross the first contour. Alternatively, according to the anatomical characteristics, a part of the second contour does not invade the first contour, and the other part thereof should be generated to be in contact with the first contour. Accordingly, by way of an embodiment example, when the first contour is generated and then the second contour is generated, the control unit 114 may perform a correction in such a manner that the second contour does not cross the already generated first contour and partial regions of the second contour are in contact with the already generated first contour.

Specifically, as to the anatomical characteristics of the heart, there should be no overlapped region between the left ventricle and the right ventricle of the heart as described above, and partial regions thereof are in contact with one another so that there should be no empty region. In addition, the inner wall of the left ventricle should be positioned within the outer wall of the left ventricle, and the inner wall of the right ventricle should be positioned within the outer wall of the right ventricle. In addition, partial regions of the inner wall of the right ventricle and the outer wall of the right ventricle should be in contact with each another.

By way of an example, in a case of the abdomen, the liver, the stomach, and the spleen located in the abdomen should not be overlapped with one another. By way of an example, when one or more tumors are present within an organ, the tumors should be located within the organ. Thus, the control unit 114 may correct the contour for each organ by reflecting the anatomical characteristics between organs. In this instance, when the manual separation process is performed, the input unit 111 may receive from a user an organ or internal tissue to be separated. Thus, the control unit 114 may determine the organ or internal tissue to be separated and correct the contour based on the anatomical characteristics of the determined organ or internal tissue to be separated.

By way of an example, when the automatic separation process is performed, the control unit 114 may analyze a variety of factors such as the appearance of each organ, the relative positional relationship between the organs, and the like from the medical image, and determine the organ included in the medical image. Thus, the control unit 114 may correct the contour based on the determination result by reflecting the characteristics of each organ.

For example, the control unit 114 may correct the contour of the organ in such a manner that the contour of the corresponding organ and the contour of one or more other organs located in the vicinity of the corresponding organ are in contact with one another. In a case of the medical image obtained by imaging the abdominal region as described above, the liver and the stomach, and the stomach and the spleen may be overlapped with each other, and partial regions thereof may be in contact with one another. Thus, the control unit 141 may perform correction in such a manner that the contours of some areas between the liver and the stomach, and the stomach and the spleen are in contact with one another while the contour between the liver and the stomach and the contour between the stomach and the spleen are not overlapped with each other.

By way of an example, when the contour of an organ and the contour of one or more organs located in its vicinity are overlapped with one another, the control unit 114 may correct the contour according to a separation distance set by a user. When the user performs a correction in a manual manner, it is difficult to perform an accurate correction. Thus, the control unit 114 according to the disclosed embodiment may correct the contour of the organ according to the separation distance set by the user, thereby providing a more accurate correction.

In a case of the mesenchyme, the contours of the right mesenchyme and the left mesenchyme should not be overlapped with each other. In this instance, when the contours of the right mesenchyme and the left mesenchyme are overlapped with each other within the medical image, the control unit 114 may correct the contour based on the separation distance received from the user, thereby performing a more accurate correction.

By way of an example, when the contours of the organ are overlapped with one another, the control unit 114 may correct the contours according to an average separation distance between regions in the vicinity of the overlapped contour region within the medical image. That is, the control unit 114 may determine the average separation distance by calculating separation distances in the regions in the vicinity of the overlapped contour region within the medical image and correct the contour based on the determination result, thereby preventing performing an abnormal correction of the contour, and providing a contour that is more closely related to the actual condition.

By way of an example, the control unit 114 may perform a correction of the contour using characteristic data for each organ stored in the DB 113. When an overlapped region of the contours of the organs exists or an empty region due to the contours being separated from one another is not reflective of the anatomical characteristics, the control unit 114 may perform a correction using characteristic data for each organ stored in the DB 113. As an example, the control unit 114 may perform a correction of the contour using data on the average separation distance between organs, data on the average separation distance between the inner wall and the outer wall of the corresponding organ, and the like. That is, the control unit 114 may perform a correction of the contour through various methods so that the actual condition may be more accurately reflected.

According to an embodiment, data on the average separation distance between the contours of the right mesenchyme and the left mesenchyme may be stored in the DB. Thus, the control unit 114 may correct the contour between the right mesenchyme and the left mesenchyme based on the data on the average separation distance, thereby more accurately displaying the contour in the medical image.

Meanwhile, a correction of the contour may be performed when a part of the contour does not fit the anatomical characteristics. Thus, when it is determined that the entire contour is misfit with the anatomical characteristics so that the anatomical characteristics cannot be reflected in the medical image by a correction of the part of the contour alone, the control unit 114 may delete the contour itself.

For example, when information about the contour of the inner wall of the organ is received and the corresponding contour is generated, a part of the contour of the inner wall of the organ may be drawn outside the contour of the outer wall. In this instance, the control unit 114 may correct only the region in which the contour of the inner wall is drawn outside the contour of the outer wall. According to an embodiment, the control unit 114 may perform a correction of the contour through various methods such as performing a correction of the contour in such a manner that the contour of the inner wall and the contour of the outer wall are in contact with each other as described above, or performing a correction of the contour in such a manner that the contour of the inner wall is drawn inside the contour of the outer wall.

By way of an example, when the contour of the inner wall is generated based on the information about the contour of the inner wall, the entire contour of the inner wall may be drawn outside the contour of the outer wall. In this instance, the control unit 114 may delete the contour of the inner wall itself. That is, when the entire contour does not fit the anatomical characteristics, the control unit 114 may not generate the entire contour.

Meanwhile, although not illustrated in the drawings, the workstation 110 may further include a communication unit. The communication unit refers to a device that transmits and receives a variety of data to and from an external device through a wireless communication network or a wired communication network. Here, the wireless communication network refers to a communication network that transmits and receives signals containing data in a wireless manner. For example, the wireless communication network may include a Bluetooth communication network and the like as well as a 3G communication network and a 4G communication network, but is not limited thereto.

In addition, the wired communication network refers to a communication network that transmits and receives signals containing data in a wired manner. For example, the wired communication network may include a PCI (peripheral component Interconnect), a PCI-express, a USB (universe serial bus), and the like, but is not limited thereto. When the workstation 110 is separately provided in a separate place, the communication unit may be connected to the image processing unit 160 and receive a medical image. In addition, the medical image may be received through a storage medium or the like, that is, there is no limitation in a method of receiving the medical image.

Hereinafter, specific embodiments of the operation flow and correction of the contour of the medical imaging apparatus will be described.

Figure 6B:
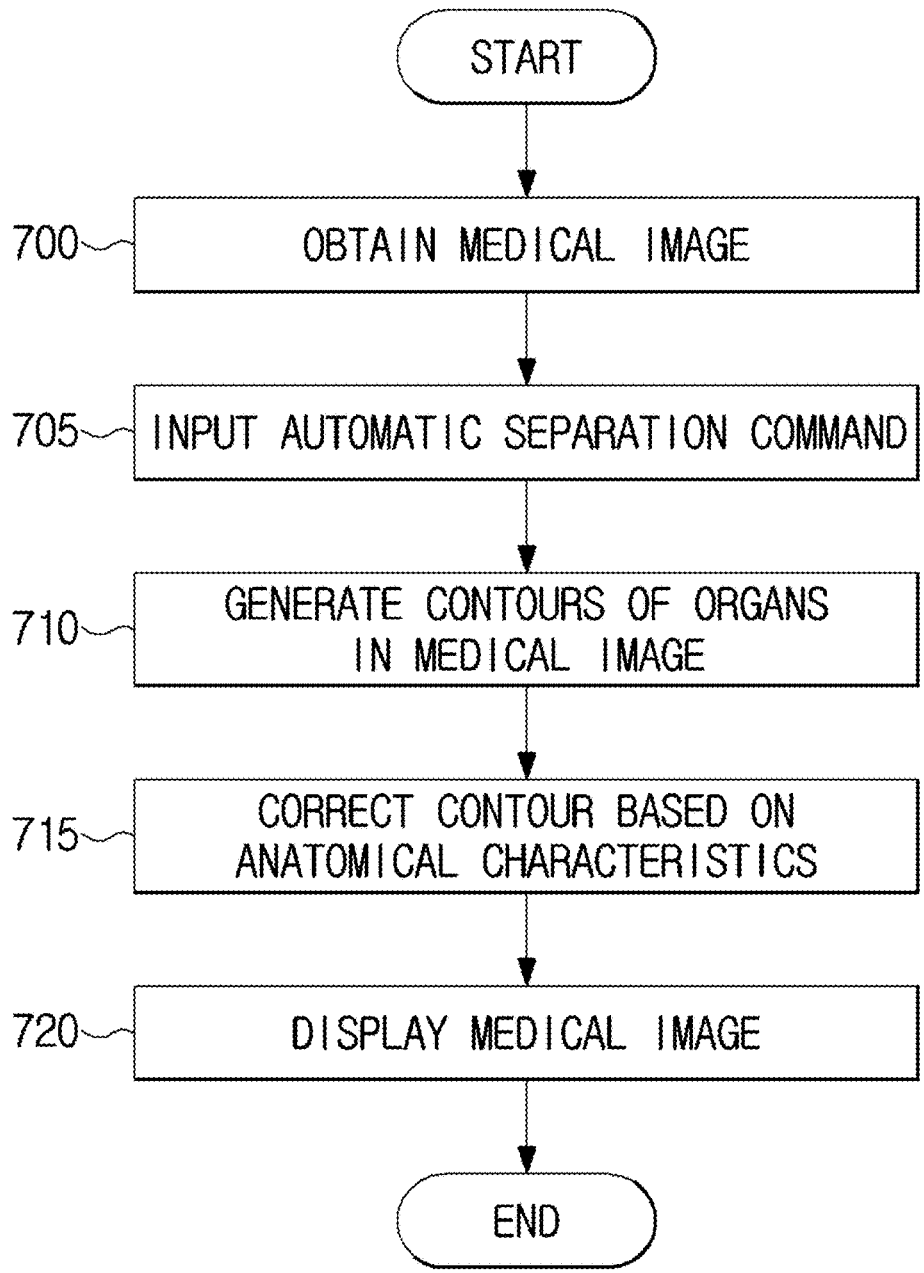
Figure 7A:
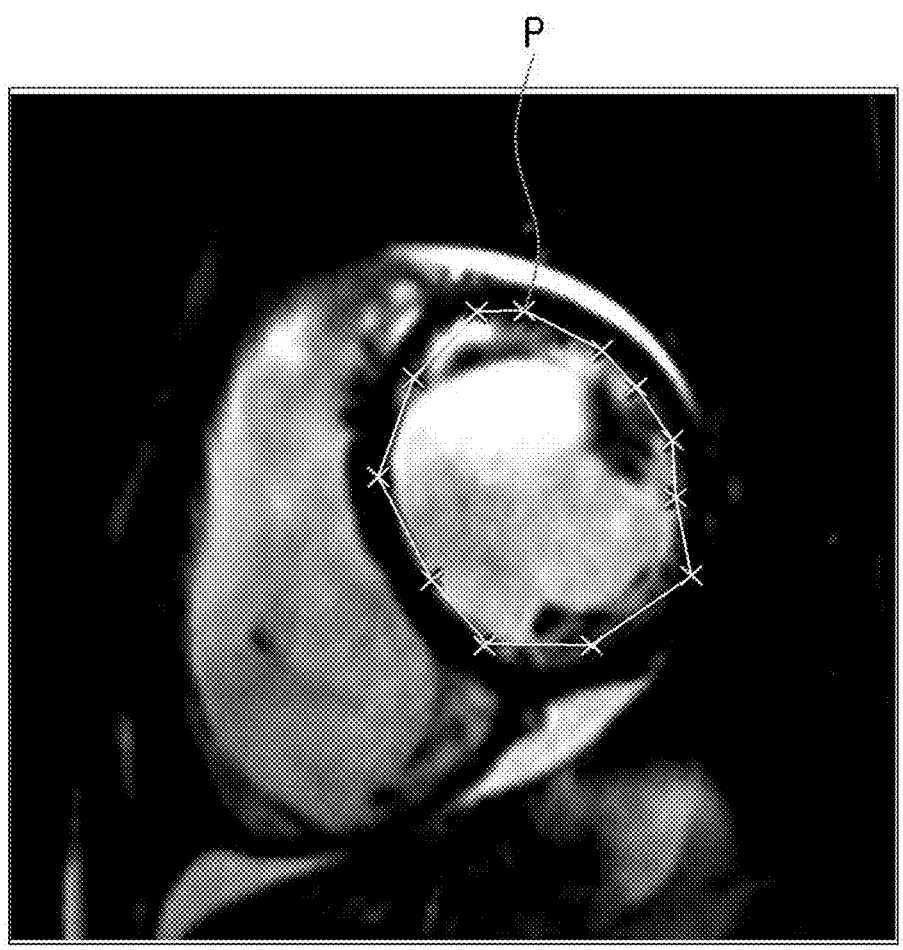
FIGS. 7A, 7B, 7C, 7D, and 7E a method of correcting a contour of the left ventricle in accordance with an embodiment of the present disclosure.
Figure 7B:
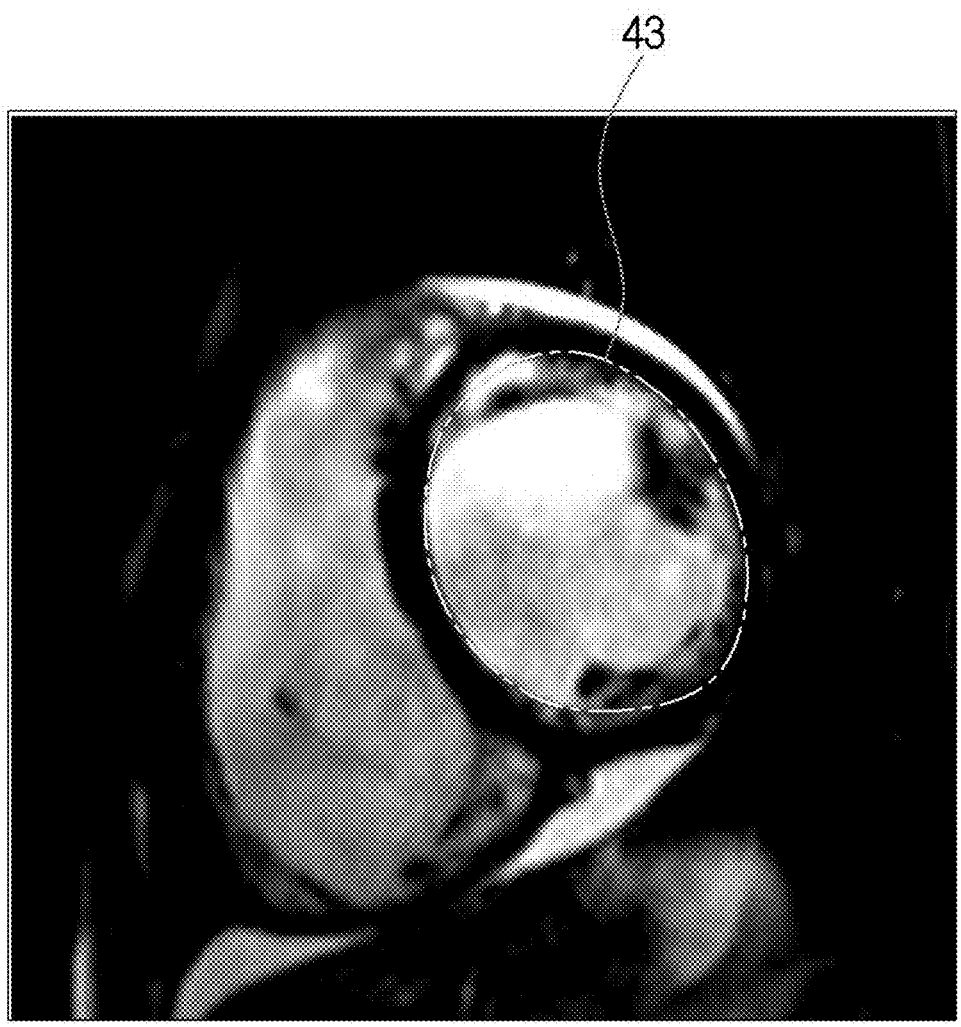
Figure 7C:
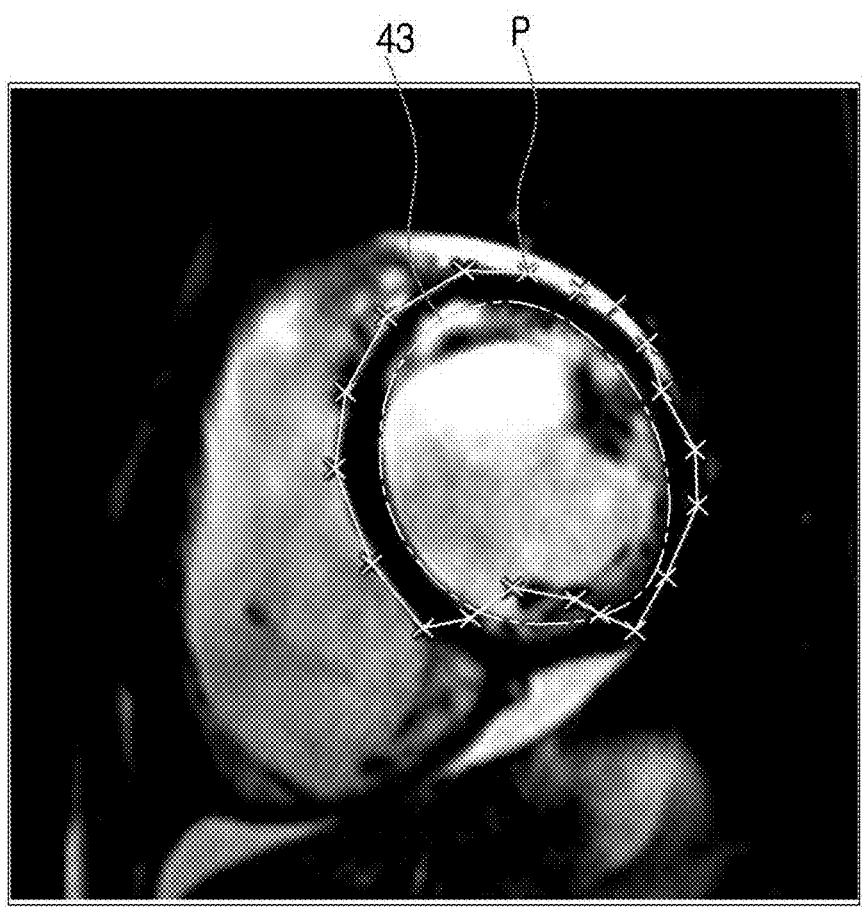
Figure 7D:
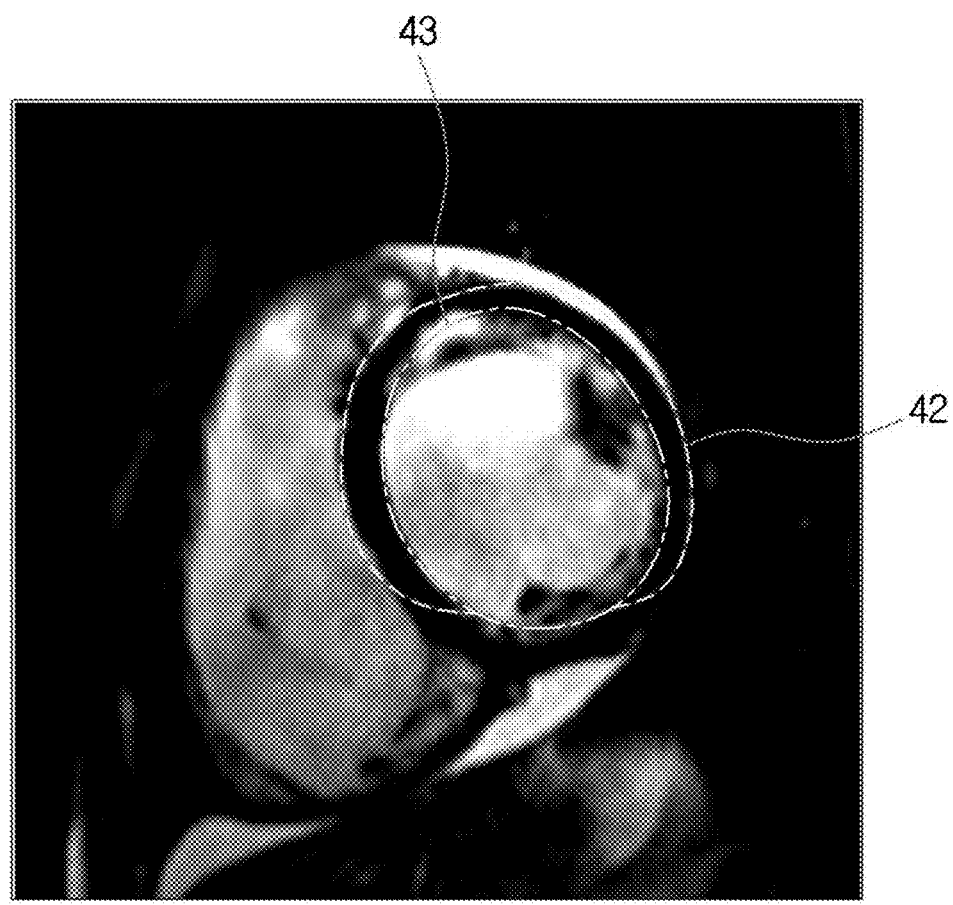
Figure 7E:
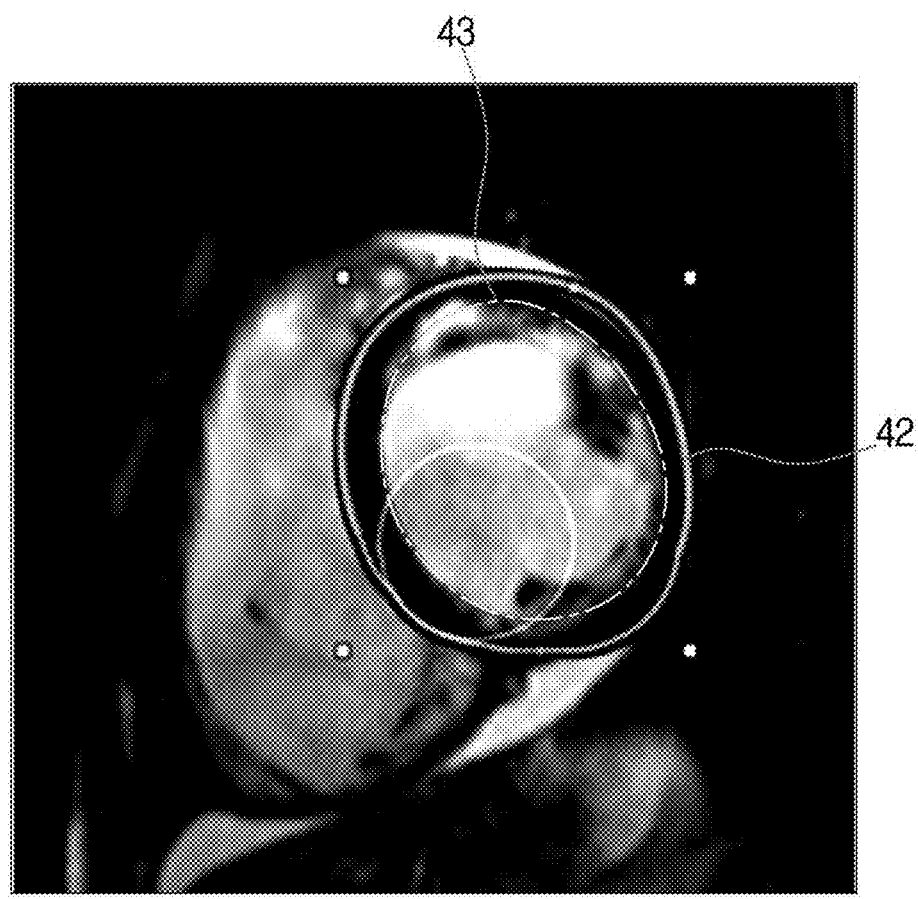
Figure 8A:
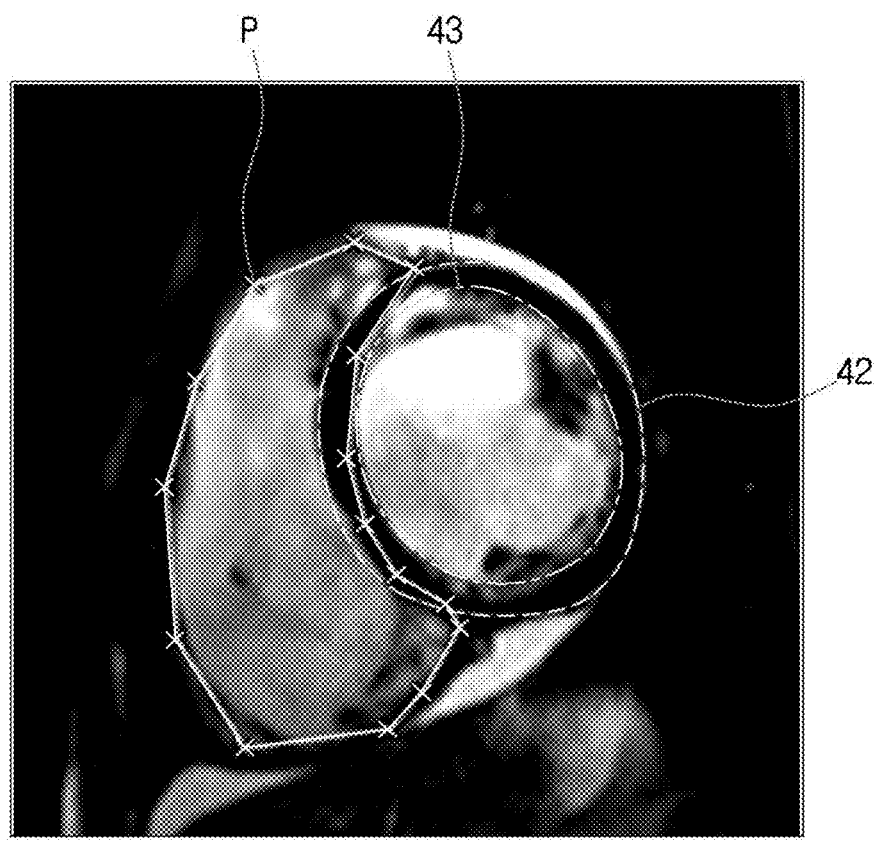
FIGS. 8A, 8B, 8C, 8D, 8E, and 8F illustrate a method of correcting a contour of the right ventricle in accordance with an embodiment of the present disclosure.
Figure 8B:
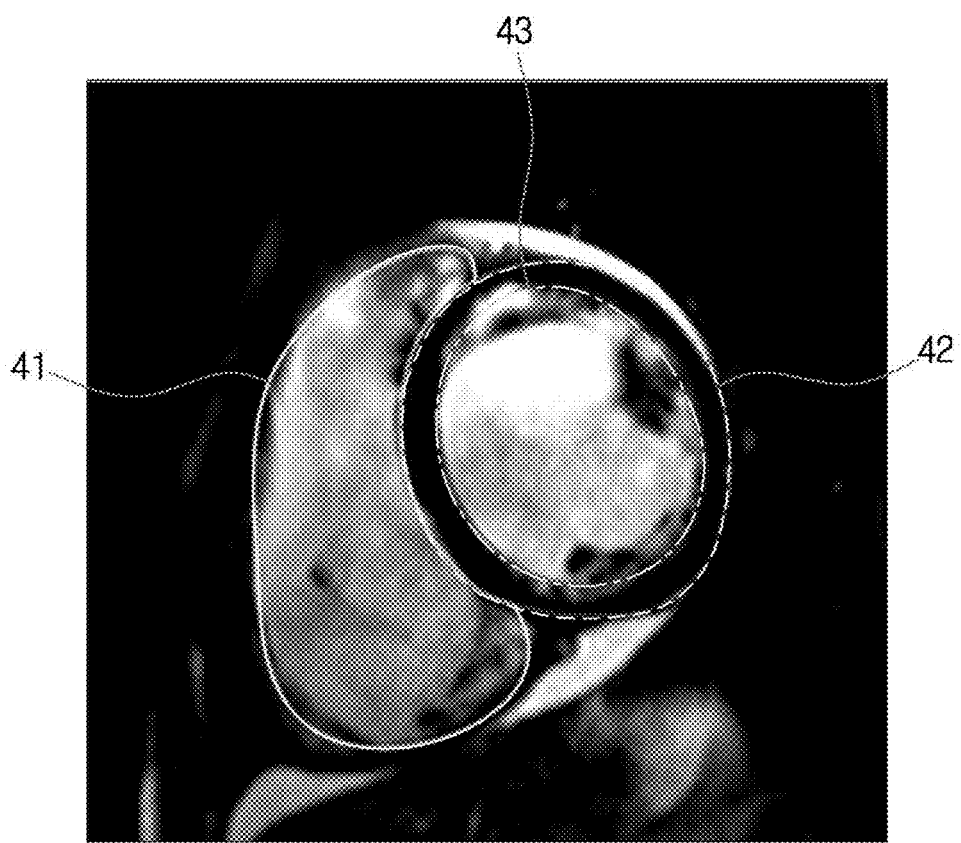
Figure 8C:
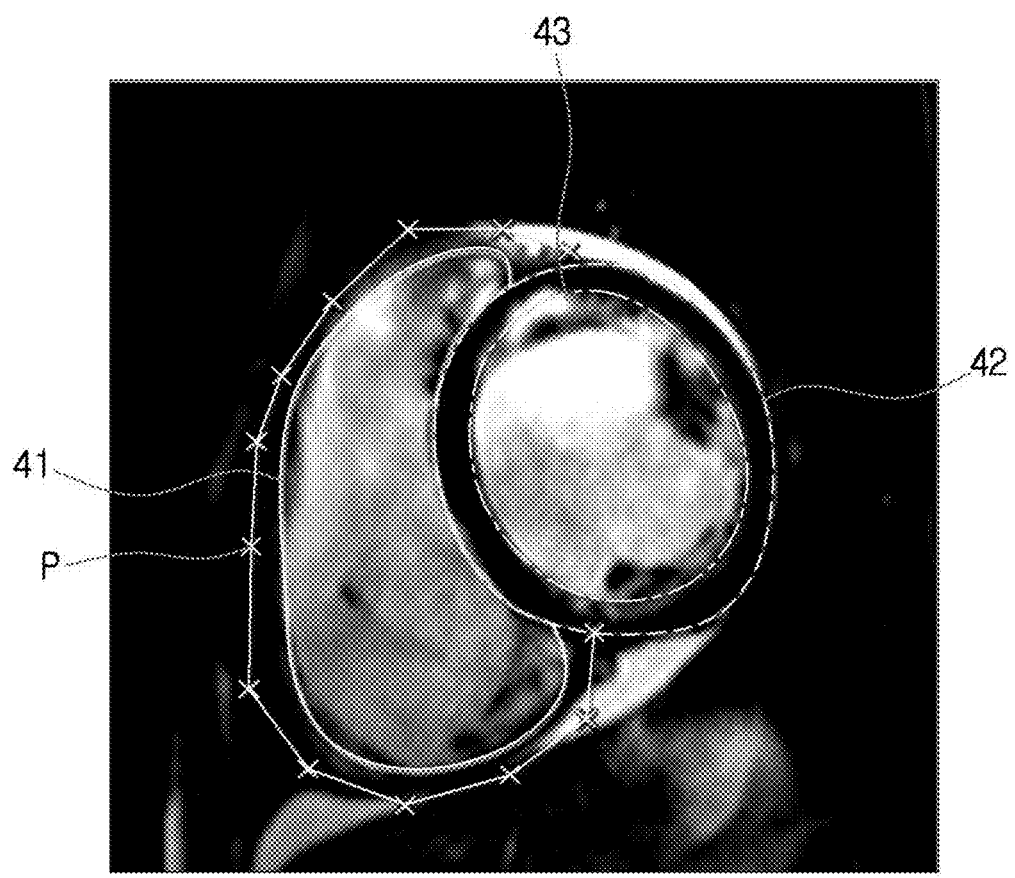
Figure 8D:
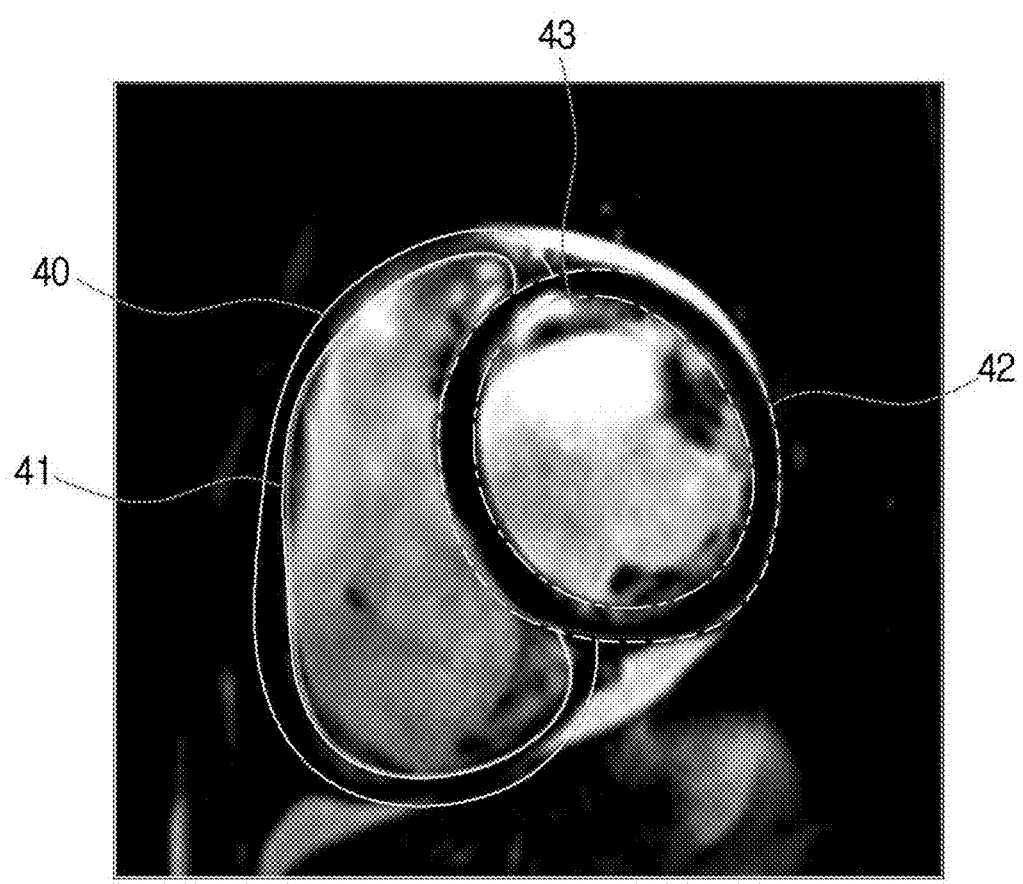
Figure 8E:
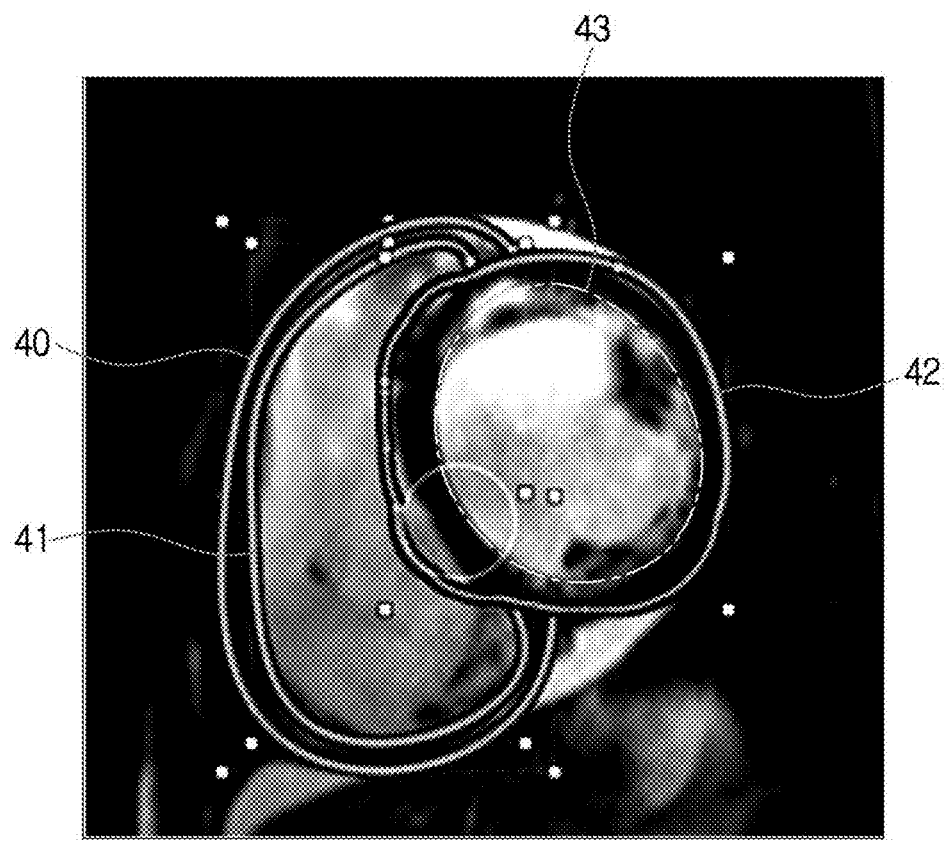
Figure 8F:
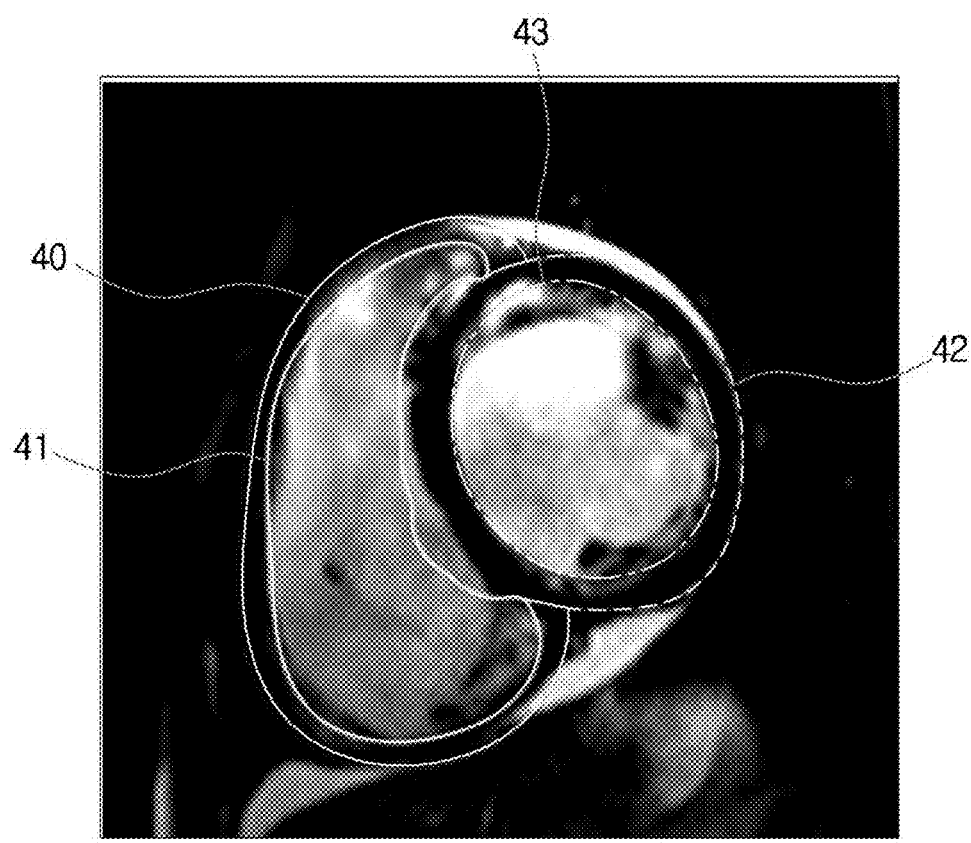
Figure 9A:
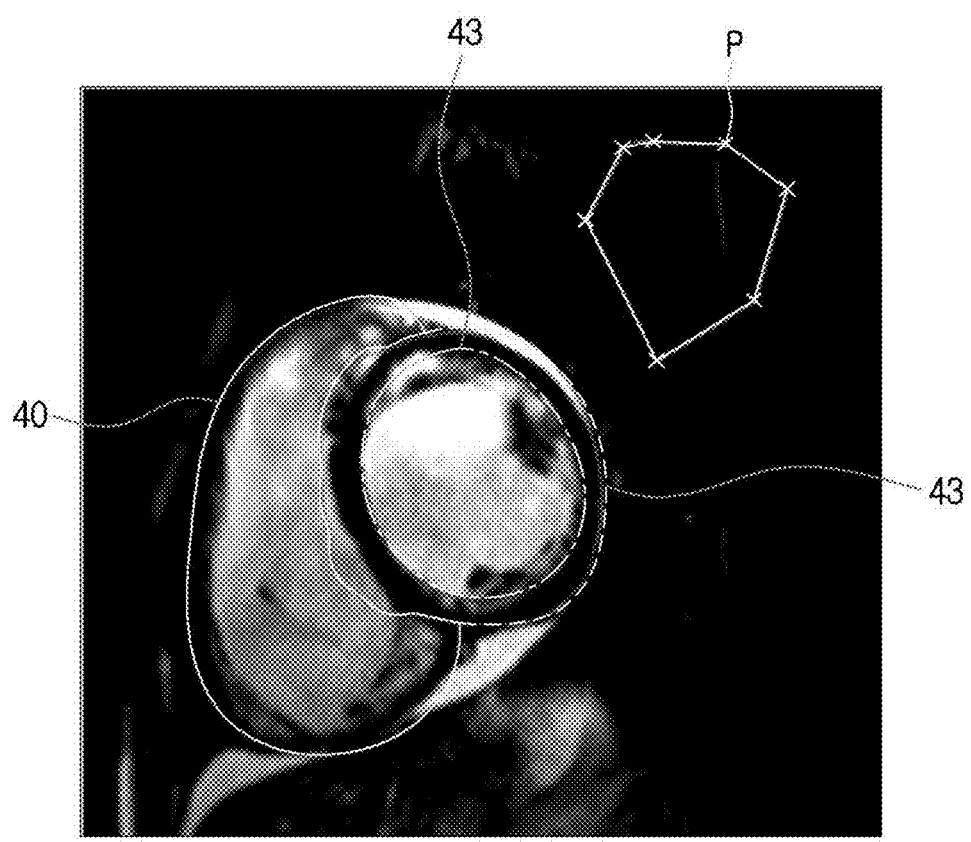
FIGS. 9A and 9B illustrate a method of correcting a contour of an inner wall of an organ when there are an inner wall and an outer wall in the organ in accordance with an embodiment of the present disclosure.
Figure 9B:
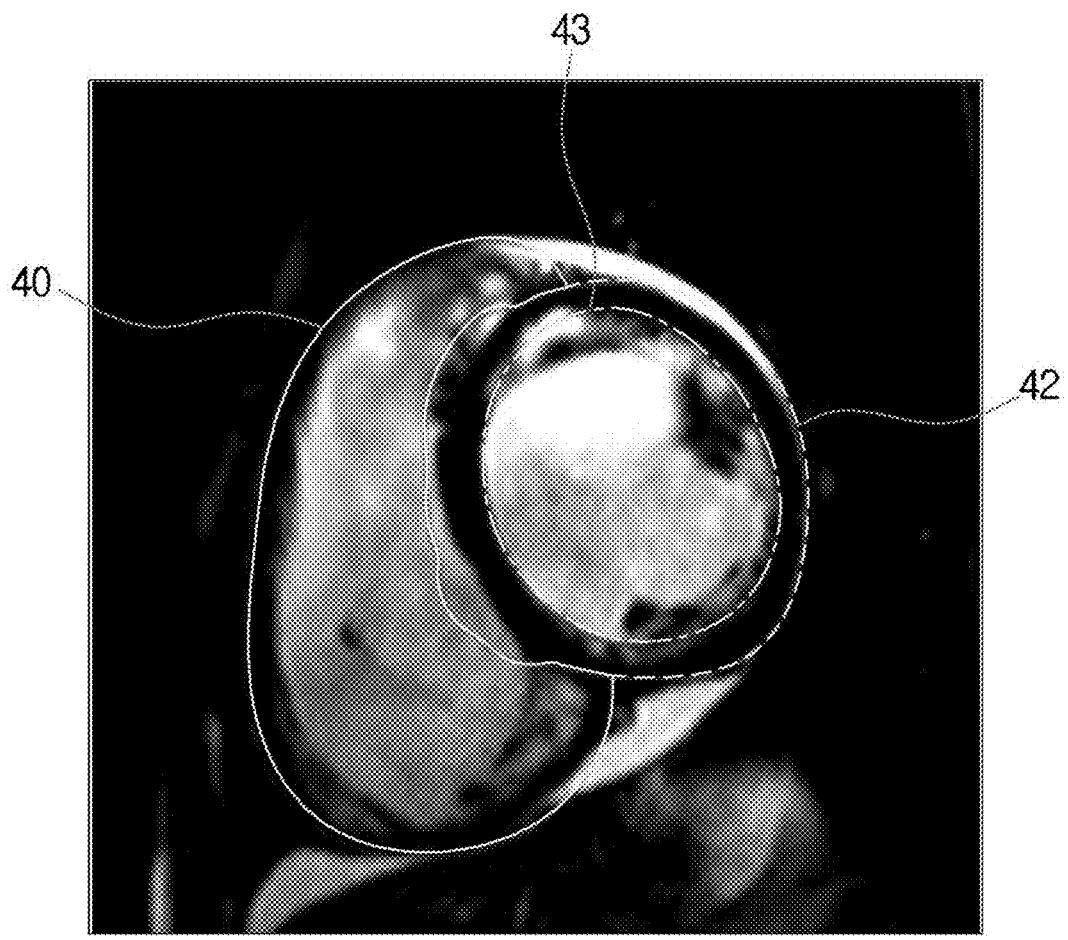

FIG. 6A is a flowchart illustrating the operation of a medical imaging apparatus according to a manual separation process, FIG. 6B is a flowchart illustrating the operation of a medical imaging apparatus according to an automatic separation process, FIGS. 7A, 7B, 7C, 7D, and 7E illustrate a method of correcting a contour of the left ventricle in accordance with an embodiment of the present disclosure, FIGS. 8A, 8B, 8C, 8D, 8E, and 8F illustrate a method of correcting a contour of the right ventricle in accordance with an embodiment of the present disclosure, FIGS. 9A and 9B illustrate a method of correcting a contour of an inner wall of an organ when there are an inner wall and an outer wall in the organ in accordance with an embodiment of the present disclosure, and FIGS. 10A, 10B, 11A, and 11B illustrate a case in which one or two contours or more are simultaneously corrected in accordance with embodiments of the present disclosure.

In operation 600, the medical imaging apparatus may obtain a medical image by imaging the inside of a subject through an imaging unit, or imager. Here, the medical image includes images obtained by imaging the inside of the subject, such as a magnetic resonance image, a computed tomography image, an ultrasonic image, and the like.

The medical imaging apparatus may receive a separation command from a user. The separation command refers to a command that requests a separation between different organs included in the medical image or a separation between internal tissues of the corresponding organ using the contour. In this instance, the separation command may include a manual separation command that generates the contour by a user inputting information about the contour and an automatic separation command that automatically generates the contour using software implemented through an automatic separation algorithm.

For example, the medical imaging apparatus may receive the separation command from the user through the above-described input unit. Accordingly, the operation of the medical imaging apparatus may vary depending on whether the separation command is the manual separation command or the automatic separation command. Hereinafter, depending on whether the manual separation command or the automatic separation command is received, the operation of the medical imaging apparatus will be individually described.

When receiving the manual separation command in operation 602, the medical imaging apparatus may receive an object desired to be separated, that is, an organ whose contour is to be generated by operation 610. In addition, the medical imaging apparatus may receive internal tissue of the organ whose contour is to be generated by operation 615. In this instance, when the corresponding organ is an organ with no internal tissue or when a contour of an outer wall of the corresponding organ is to be generated, the operation of receiving the internal tissue of the organ may be omitted. The medical imaging apparatus may determine the object to be separated by receiving the object to be separated from a user and then reflect anatomical characteristics of the received object to be separated when correcting the contour.

Meanwhile, the medical imaging apparatus may receive information about the contour from the user in operation 620. The user may input the information about the contour as points or lines.

Accordingly, in operation 625, the medical imaging apparatus may correct the contour based on the anatomical characteristics when generating the contour based on the received information about the contour. Hereinafter, a case of correcting the contour of the heart will be described.

For example, FIGS. 7A, 7B, 7C, 7D, and 7E illustrate a method of correcting the contour of the left ventricle. The medical imaging apparatus may receive information about the contour separating the received object. In this instance, the medical imaging apparatus may receive a manual separation command about the heart. In addition, the medical imaging apparatus may receive the inner wall of the left ventricle from the user as the object to be separated. Thus, the medical imaging apparatus may receive the information about the contour as described above.

FIG. 7A illustrates a case of receiving the information about the contour of the inner wall of the left ventricle in the medical image. Referring to FIG. 7A, the medical imaging apparatus may receive from the user a plurality of points (p) which are the basis for the generation of the contour. FIG. 7B illustrates the contour of the inner wall of the left ventricle generated by connecting the plurality of points. As illustrated in FIG. 7B, the medical imaging apparatus may generate the contour 43 of the inner wall of the left ventricle by connecting the plurality of points.

In addition, the medical imaging apparatus may receive a separation command about the outer wall of the left ventricle from the user. Accordingly, the medical imaging apparatus may receive the information about the contour as described above. FIG. 7C illustrates a case of receiving information about the contour of the outer wall of the left ventricle in the medical image. The medical imaging apparatus may receive from the user a plurality of points (p) which are the basis for the contour of the outer wall. In this instance, the contour 43 of the outer wall obtained by connecting the points may cross the contour of the inner wall as illustrated in FIG. 7C, and therefore it may not fit the anatomical characteristics.

Thus, as illustrated in FIG. 7D, the medical imaging apparatus according to the disclosed embodiment may perform a correction of contour in such a manner that the contour 43 of the outer wall of the left ventricle is in contact with the contour 42 of the inner wall. However, a method of correcting the contour is not limited to a method illustrated in the drawings, and the contours may be corrected by a separation distance as describe above, that is, there is no limitation in the method of correcting the contour.

In this instance, as illustrated in FIG. 7E, the medical imaging apparatus according to an embodiment may select the contour of the outer wall and then correct the contour of the outer wall using a circle mask tool. In addition, the medical imaging apparatus may perform a correction of the contour using a variety of already known manual correction tools. In addition, as will be described later, the medical imaging apparatus according to the disclosed embodiment may simultaneously correct a plurality of overlapped contours or a plurality of contours selected by a user, thereby increasing user convenience. This will be described in detail later.

Meanwhile, the medical imaging apparatus may receive a manual separation command for the inner wall of the right ventricle. Accordingly, as illustrated in FIG. 8A, the medical imaging apparatus may receive a plurality of points (p) indicating the contour of the inner wall. In this instance, when the contour of the inner wall of the right ventricle is drawn by connecting the plurality of points (p), the contours 42 and 43 of the inner wall and outer wall of the left ventricle are overlapped with each other as illustrated in FIG. 8A, and therefore it may not fit the anatomical characteristics. Accordingly, as illustrated in FIG. 8B, the medical imaging apparatus according to the disclosed embodiment may correct the contour 41 of the inner wall of the right ventricle so as not to be overlapped with the contour 42 of the outer wall of the left ventricle and the contour 43 of the inner wall of the left ventricle.

In addition, as illustrated in FIG. 8C, the medical imaging apparatus may receive a plurality of points (p) for the outer wall of the right ventricle. In this instance, according to the anatomical structure, partial regions between the outer wall of the left ventricle and the outer wall of the right ventricle are in contact with each other. Accordingly, the medical imaging apparatus according to the disclosed embodiment may generate the contour 40 of the outer wall of the right ventricle to be in contact with the contour 42 of the outer wall of the left ventricle as illustrated in FIG. 8D, although the points for the contact region have not been received.

Meanwhile, the medical imaging apparatus may provide a manual correction tool for the contour. In this instance, the user may correct each contour or simultaneously select and correct a plurality of contours.

Referring to FIG. 8E, the user may simultaneously select the contours 42 and 43 of the outer wall and inner wall of the right ventricle and the contour 40 of the outer wall of the left ventricle. Accordingly, the user may simultaneously correct the three contours using the circle mask.

For example, when the user drags the contour 42 of the outer wall of the left ventricle toward the inside of the right ventricle using the circle mask, the medical imaging apparatus may correct the contours 40 and 41 of the outer wall and inner wall of the right ventricle inward while correcting the contour 42 of the outer wall of the left ventricle toward the inside of the right ventricle. Accordingly, as illustrated in FIG. 8F, the medical imaging apparatus may correct the contours in such a manner that the contours 42 and 43 of the inner/outer walls of the left ventricle and the contours 42 and 43 of the inner/outer walls of the right ventricle are not overlapped with each other.

Meanwhile, the internal tissue of the organ should not be drawn outside the organ. Accordingly, when a part of the contour of the internal tissue of the organ is drawn outside the organ or when the entire contour is drawn outside the organ, the medical imaging apparatus may correct this.

For example, FIG. 9A illustrates a case in which a plurality of points (p) for the contour of the inner wall of the right ventricle are all drawn outside the contour of the outer wall of the right ventricle. In this instance, as illustrated in FIG. 9B, the medical imaging apparatus may not generate the contour of the inner wall of the right ventricle.

Figure 10A:
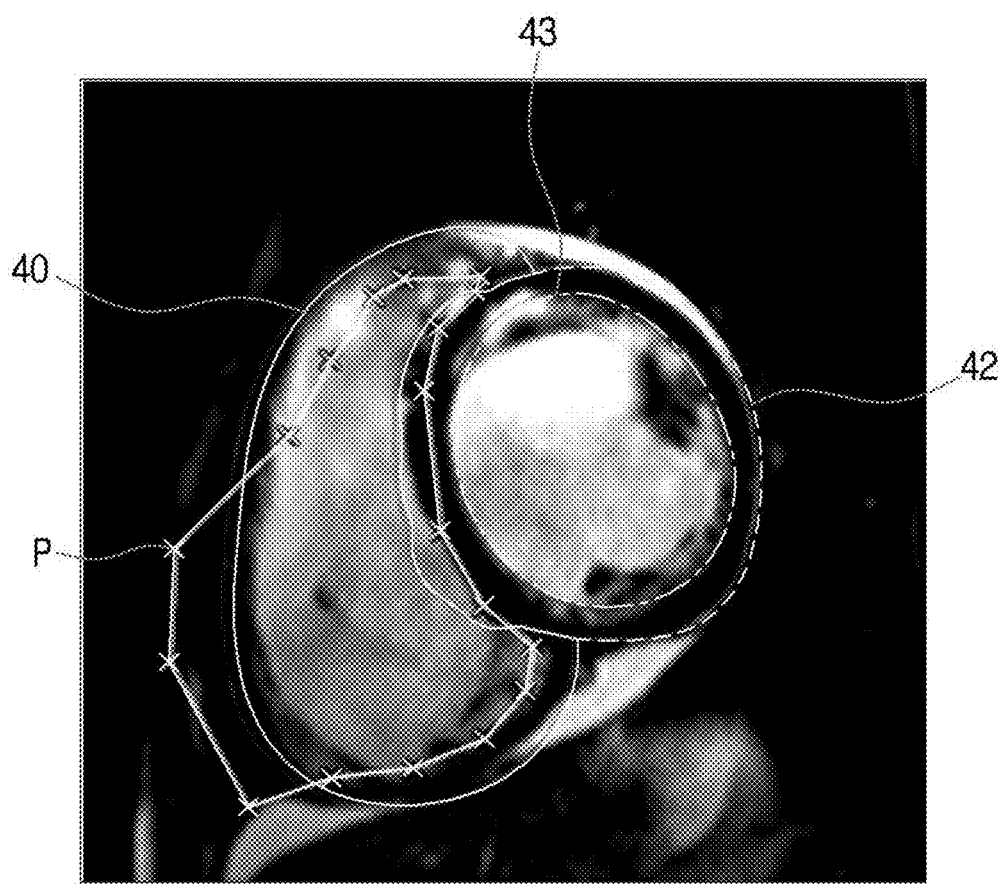
FIGS. 10A, 10B, 11A, and 11B illustrate a case in which one or two contours or more are simultaneously corrected in accordance with an embodiment of the present disclosure.
Figure 10B:
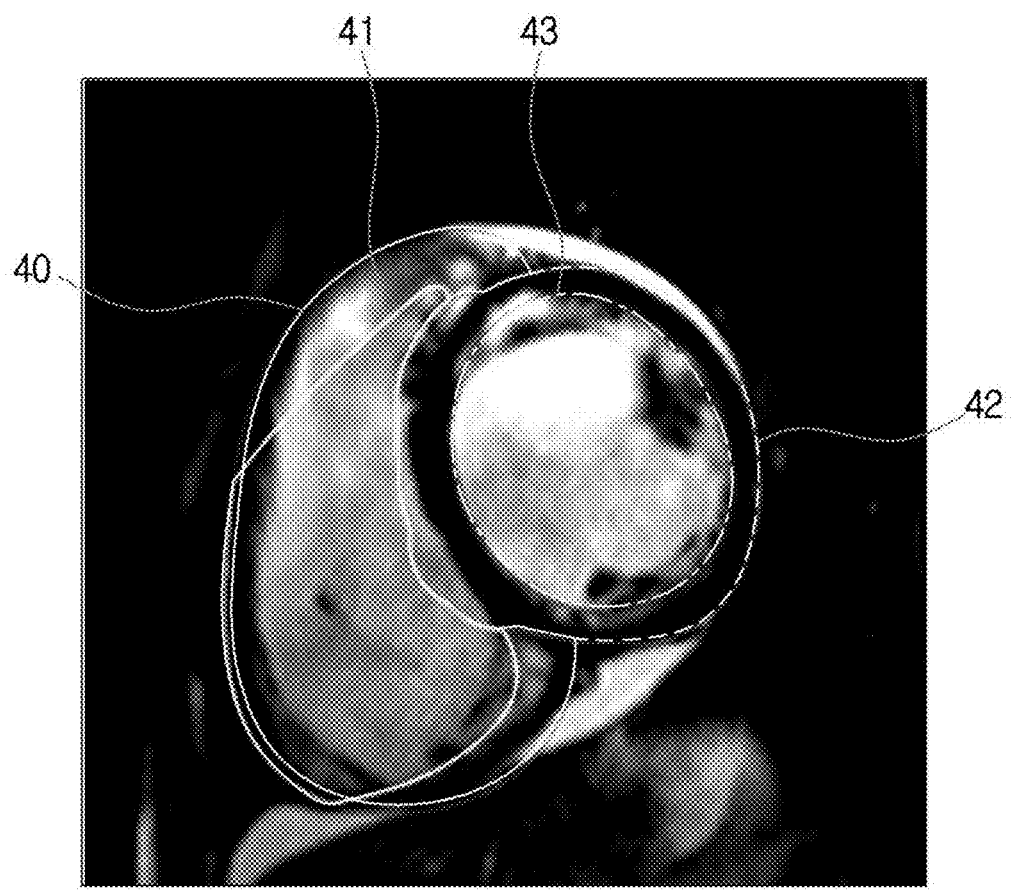

By way of an example, FIG. 10A illustrates a case in which the plurality of points (p) for the contour of the inner wall of the right ventricle are partially drawn outside the contour of the outer wall of the right ventricle. In this instance, the medical imaging apparatus may perform a correction of the contour in such a manner that only points input outside the contour 40 of the outer wall of the right ventricle among the plurality of points (p) are in contact with the contour 40 of the outer wall of the right ventricle, thereby generating the contour 41 of the inner wall of the right ventricle as illustrated in FIG. 10B. Accordingly, there is no overlapped region between the contours 40 and 41 of the outer wall and inner wall of the right ventricle and the contours 42 and 43 of the outer wall and the inner wall of the left ventricle.

Meanwhile, the user may select only one contour among the plurality of contours and manually correct the selected contour as described above. In this instance, the medical imaging apparatus may provide the manual correction tool so that the anatomical characteristics can be reflected.

Figure 11A:
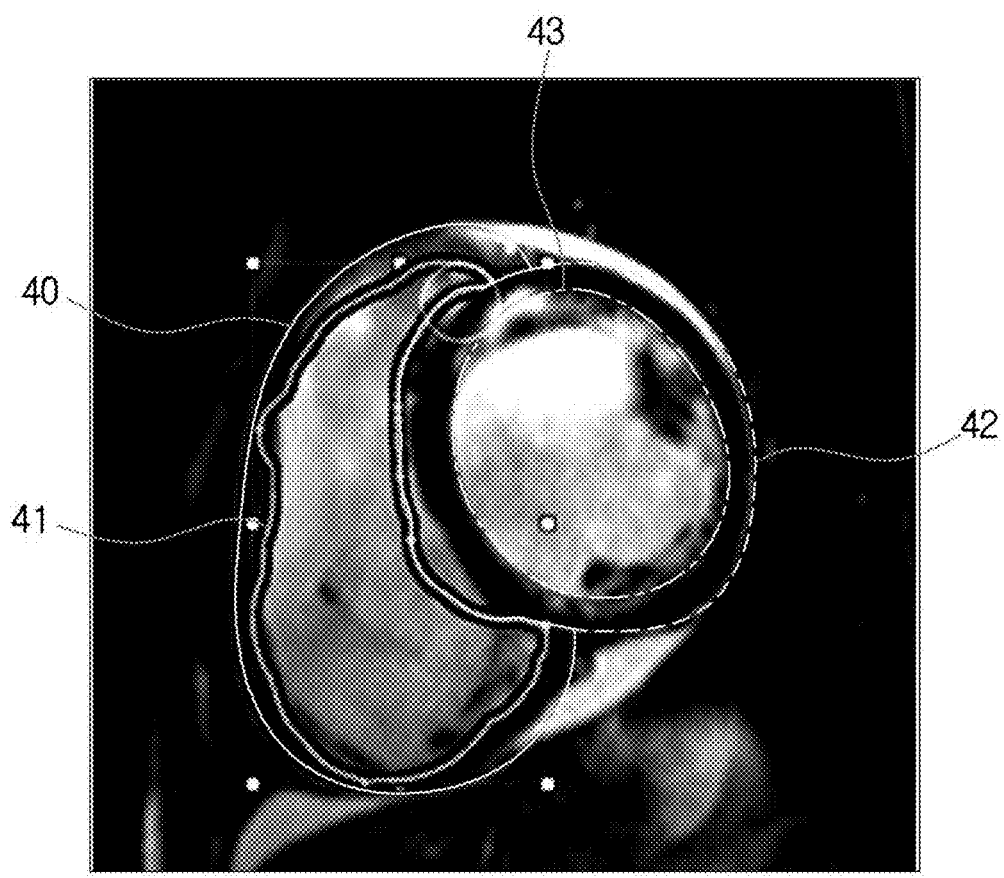

For example, FIG. 11A illustrates a case in which a user selects the contour of the inner wall of the right ventricle and manually corrects the selected contour. Referring to FIG. 11A, the user may adjust the contour 41 of the inner wall of the right ventricle using the circle mask. In this instance, when the contour 41 of the inner wall of the right ventricle is overlapped with the contour 42 of the outer wall of the right ventricle using the circle mask, it does not fit the anatomical characteristics.

Figure 11B:
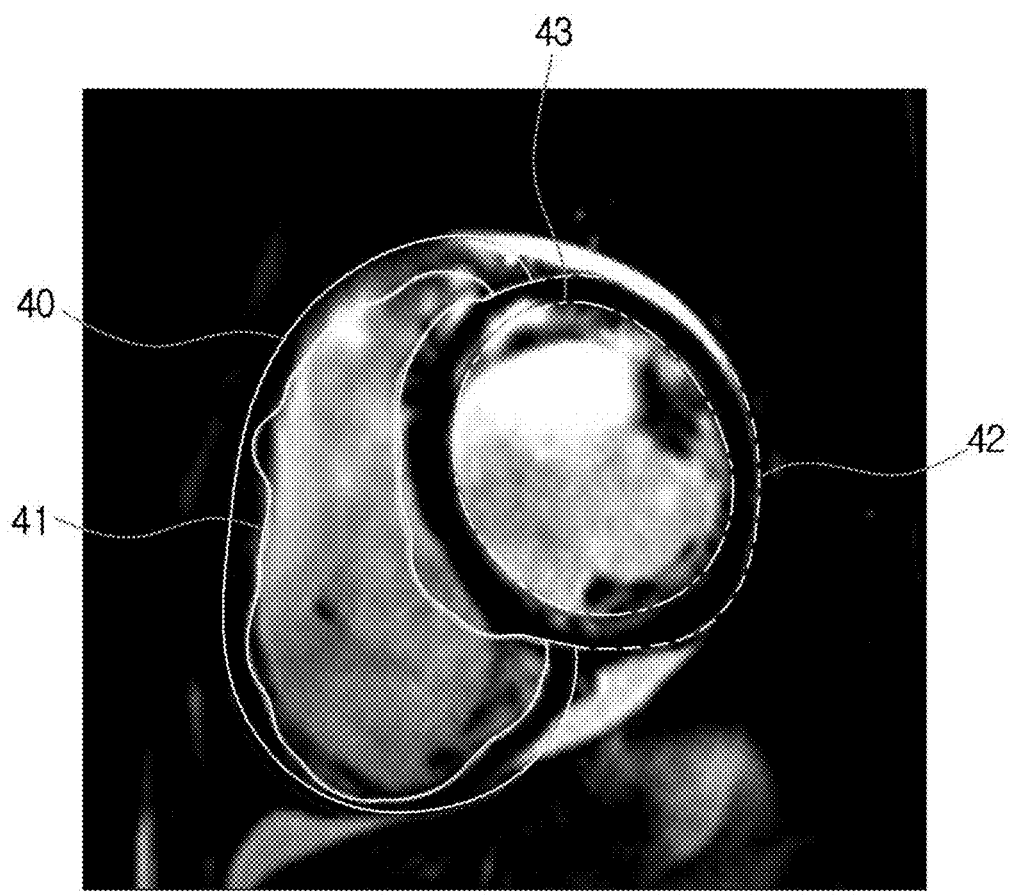

Thus, the medical imaging apparatus according to the disclosed embodiment may perform a manual correction only within a range in which the contour 41 of the inner wall of the right ventricle is not outside the contour 40 of the outer wall of the right ventricle, thereby preventing the occurrence of an error caused by the manual correction. Accordingly, as illustrated in FIG. 11B, the medical imaging apparatus may generate the corresponding contour in such a manner that there is no overlapped region between the contours 40 and 41 of the outer wall and inner wall of the right ventricle and the contours 42 and 43 of the outer wall and inner wall of the left ventricle.

In operation 630, the medical imaging apparatus may display the medical image whose contour has been corrected through a display unit. Accordingly, the user may quantitatively analyze the corresponding organ using the contour drawn in the medical image, thereby performing a diagnosis of the corresponding organ. Hereinafter, the operation flow of the medical imaging apparatus according to the automatic separation will be described.

Meanwhile, in operation 700, the medical imaging apparatus may obtain the medical image. The operation 700 is the same as the above-described operation 600, and thus a detailed description thereof will be omitted.

As described above, the operation of the medical imaging apparatus may vary depending on whether the manual separation command or the automatic separation command is received. When the automatic separation command is received in operation 705, the medical imaging apparatus may generate the contour of one or more organs included in the medical image in operation 710. However, the medical imaging apparatus may generate the contour by performing an automatic separation process although the automatic separation command has not been separately received from the user, such as by a user setting etc., and there is no limitation in the method of generating the contour.

For example, the medical imaging apparatus may determine one or more organs included in the medical image through software implemented through the automatic separation algorithm, and generate the contour in consideration of the determination result. The medical imaging apparatus may generate the contour separating organs through a variety of already known separation methods, and there is no limitation in this.

In this instance, in operation 715, the medical imaging apparatus may correct the contour in consideration of the anatomical characteristics. The correction method is the same as the above-described correction method, and thus description thereof will be omitted.

In operation 720, the medical imaging apparatus may display the corrected medical image through the display unit. Accordingly, the user may quantitatively analyze the organ using the contour drawn in the medical image, thereby performing diagnosis of the organ.

Figure 12A:
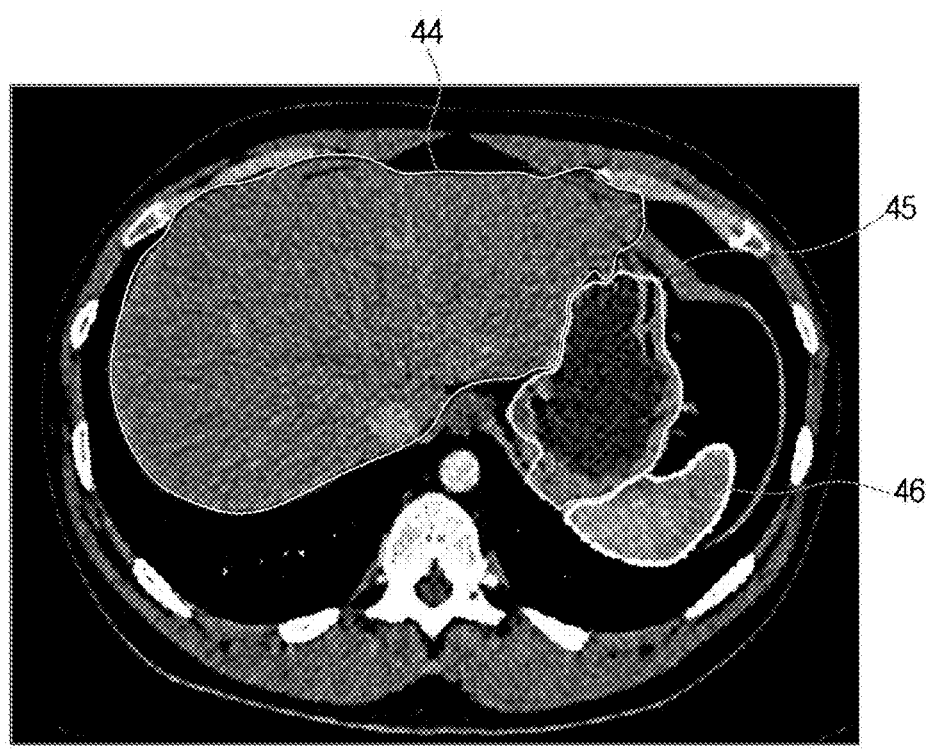
FIGS. 12A and 12B illustrate a medical image of an abdominal region in which contours of a plurality of organs are drawn in accordance with an embodiment of the present disclosure.
Figure 12B:
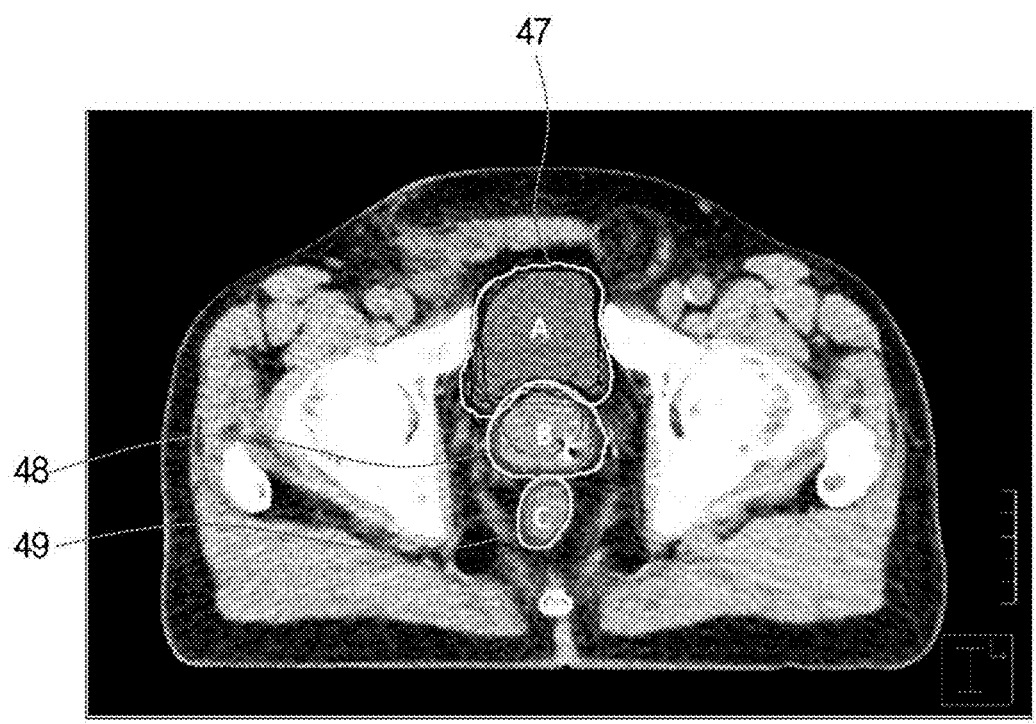
Figure 13:
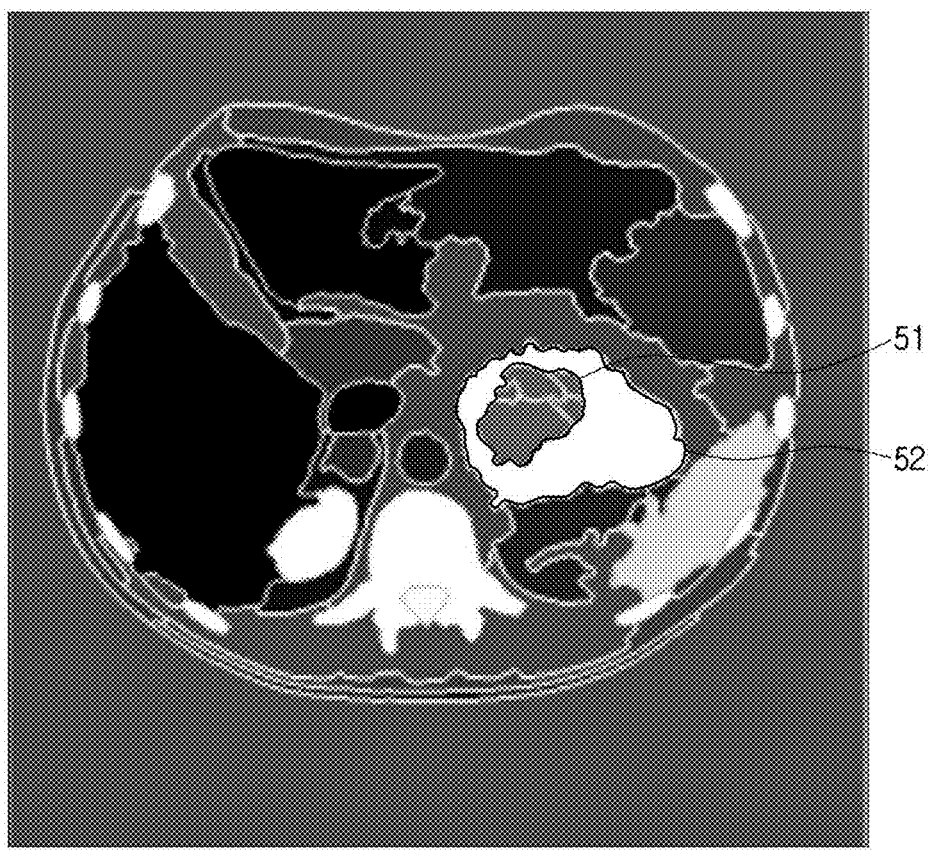
FIG. 13 illustrates a medical image of an abdominal region in which contours of an organ and internal tissues of the organ are drawn.

FIGS. 12A and 12B illustrate a medical image of an abdominal region in which contours of a plurality of organs are drawn in accordance with an embodiment of the present disclosure, and FIG. 13 illustrates a medical image of an abdominal region in which contours of an organ and internal tissue of the organ are drawn.

As described above, the medical imaging apparatus may include all types of apparatuses that can obtain the medical image by imaging the inside of the subject. Thus, the medical image includes all images including image information about the inside of the subject, such as an MRI image, a CT image, an ultrasonic image, and the like. The medical images illustrated in FIGS. 12A, 12B, and 13 are CT images obtained by a CT apparatus.

When imaging the abdomen of the subject, the medical imaging apparatus may obtain a CT image including various organs such as the bladder, the prostate, the rectum, the liver, the stomach, the spleen, etc. In this instance, the medical imaging apparatus may generate the corresponding contour in such a manner that the contours of different organs are not overlapped with one another. For example, the medical image illustrated in FIG. 12A includes organs such as the liver, the stomach, the spleen, etc. In this instance, the contours of different organs such as the liver, the stomach, or the spleen are overlapped with one another, and thus it is difficult to obtain accurate diagnosis of the above-described organ. Thus, as illustrated in FIG. 12A, the medical imaging apparatus may generate the contour in such a manner that the contour 44 of the liver, the contour 45 of the stomach, and the contour 46 of the spleen are not overlapped with one another.

By way of an example, as illustrated in FIG. 12B, the medical imaging apparatus may generate the contour in such a manner that a contour 47 of the bladder A, a contour 48 of the prostate B, and a contour 49 of the rectum C are not overlapped with one another. By way of an example, the medical image illustrated in FIG. 13 may include the stomach, and a tumor may be present inside the stomach. In this instance, when the contour of the tumor and the contour of the stomach are overlapped with each other, the medical imaging apparatus may correct the contour 51 of the tumor in such a manner that the contour 51 of the tumor is not drawn outside the contour 52 of the stomach as illustrated in FIG. 13.

That is, the medical imaging apparatus according to the disclosed embodiment may perform correction of all organs inside the subject and perform correction for all different types of medical images.

The embodiments set forth in the present specification and the components illustrated in the drawings are merely examples, and there may be various modifications that can replace the embodiments and the drawings of the present specification at the application time of the present application.

It should be understood, however, that there is no intent to limit the disclosure to the particular forms disclosed, but on the contrary, the disclosure is to cover all modifications, equivalents, and alternatives falling within the spirit and scope of the disclosure.

Terms used in the present specification are intended to illustrate the embodiments and are not intended to limit the disclosure. In addition, as used herein, the singular forms "a", "an", and "the" are intended to include the plural forms, including "at least one", unless the content clearly indicates otherwise. In the specifications, it should be understood that the terms "comprising" or "including" when used in these specifications, specify the presence of stated features, items, steps, operations, elements, and/or components but do not preclude the presence or addition of one or more other features, items, steps, operations, elements, components, and/or groups thereof. In the drawings, like reference numerals refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

In the following description, terms such as "unit", "block", "member", "module" and the like may indicate a unit for processing at least one function or operation. For example, the terms may indicate software and hardware such as FPGA or ASIC. However, the terms such as "unit", "block", "member", "module" and the like are not limited to a software and hardware, and the "unit", "block", "member", "module" and the like may be components that can be stored in an accessible storage medium and performed by one or more processors.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An apparatus comprising:
   an interface configured to receive information about a first contour defining a first tissue in an image and a second contour defining a second tissue in the image; and
   a controller configured to perform a correction on at least one of the first contour and the second contour such that the first contour and the second contour do not cross each other, based on the received information,
   wherein the controller performs the correction such that the first contour and the second contour are in contact with one another based on anatomical characteristics of at least one of the first tissue and the second tissue.

2. The apparatus according to claim 1, wherein the controller performs the correction based on at least one of anatomical characteristics of at least one of the first tissue and the second tissue, and such that a part of the second contour is in contact with the first contour.

3. The apparatus according to claim 1, wherein
   the first tissue includes an inner wall of an organ and the second tissue includes an outer wall of the organ, and
   the first contour defines the inner wall of the organ and the second contour defines the outer wall of the organ.

4. The apparatus according to claim 3, wherein the controller performs the correction on the first contour defining the inner wall of the organ such that the first contour defining the inner wall of the organ does not cross the second contour defining the outer wall of the organ.

5. The apparatus according to claim 4, wherein, when the first contour defining the inner wall of the organ is drawn entirely outside the second contour defining the outer wall of the organ, the controller performs a correction by deleting the first contour defining the inner wall of the organ.

6. The apparatus according to claim 1, wherein the controller is configured to perform a correction based on a separation distance received by the interface.

7. The apparatus according to claim 1, wherein the controller is configured to perform a correction based on at least one of an average separation distance between the first contour and the second contour in the image, and an average separation distance of the first tissue and the second tissue stored in a database.

8. The apparatus according to claim 4, wherein the controller is configured to perform a correction on the first contour defining the inner wall of the organ based on a separation distance received by the interface.

9. The apparatus according to claim 4, wherein the controller is configured to perform a correction based on at least one of an average separation distance between the first contour and the second contour in the image, and an average separation distance stored in a database.

10. An apparatus comprising:
    a controller configured to perform a correction on at least one of a first contour defining a first tissue in an image in which the first contour is generated according to an automatic separation and a second contour defining a second tissue in the image in which the second contour is generated according to the automatic separation such that the first contour and the second contour are not overlapped with one another; and
    a display configured to display the image corrected by the controller,
    wherein the controller performs the correction such that the first contour and the second contour are in contact with one another based on anatomical characteristics of at least one of the first tissue and the second tissue.

11. The apparatus according to claim 10, wherein, the controller performs the correction on the first contour and the second contour, or performs the correction on a selected contour of one of the first contour and the second contour.

12. The apparatus according to claim 10, wherein the controller performs the correction such that the first contour and the second contour are in contact with one another based on a predetermined separation distance.

13. The apparatus according to claim 10, wherein the controller performs the correction based on at least one of anatomical characteristics of at least one of the first tissue and the second tissue, and such that a part of the second contour is in contact with the first contour.

14. The apparatus according to claim 10, wherein the controller performs the correction based on at least one of a separation distance received by a interface, an average separation distance between the first contour and the second contour in the image, and an average separation distance of the first tissue and the second tissue stored in a database.

15. The apparatus according to claim 10, wherein the first tissue includes an inner wall of an organ and the second tissue includes an outer wall of the organ, and the first contour defines the inner wall of the organ and the second contour defines the outer wall of the organ, and the controller performs the correction such that the first contour defining the inner wall of the organ does not cross the second contour defining the outer wall of the organ.

16. The apparatus according to claim 15, wherein, when the first contour defining the inner wall of the organ is drawn entirely outside the second contour defining the outer wall of the organ, the controller performs the correction by deleting the first contour defining the inner wall of the organ.

17. The apparatus according to claim 15, wherein the controller performs the correction based on a separation distance.

18. The apparatus according to claim 15, wherein the controller performs the correction based on at least one of an average separation distance between the first contour and the second contour in the image, and an average separation distance stored in a database.

19. A medical imaging apparatus comprising:
    an imager configured to obtain an image;
    a controller configured to perform a correction on at least one of a first contour defining a first tissue in the image in which the first contour is generated according to an automatic separation and a second contour defining a second tissue in the image in which the second contour is generated according to an automatic separation such that the first contour and the second contour are not overlapped with one another; and
    a display configured to display the image corrected by the controller,
    wherein the controller performs the correction such that the first contour and the second contour are in contact with one another based on anatomical characteristics of at least one of the first tissue and the second tissue.

* * * * *